(12) United States Patent
Fey et al.

(10) Patent No.: US 11,332,435 B2
(45) Date of Patent: May 17, 2022

(54) METHOD FOR PRODUCING (3S)-3-(4-CHLORO-3-{[(2S,3R)-2-(4-CHLOROPHENYL)-4,4,4-TRIFLUORO-3-METHYLBUTANOYL]AMINO}PHENYL)-3-CYCLO-PROPYLPROPANOIC ACID AND THE CRYSTALLINE FORM THEREOF FOR USE AS A PHARMACEUTICAL INGREDIENT

(71) Applicant: Bayer Pharma Aktiengesellschaft, Berlin (DE)

(72) Inventors: Peter Fey, Wuppertal (DE); Philipp Rubenbauer, Bensheim (DE); Kai Lovis, Dusseldorf (DE); Britta Olenik, Bottrop (DE); Julia Kusel, Bochum (DE); Felix Spindler, Starrkirch-Wil (CH)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 16/767,724

(22) PCT Filed: Nov. 26, 2018

(86) PCT No.: PCT/EP2018/082526
§ 371 (c)(1),
(2) Date: May 28, 2020

(87) PCT Pub. No.: WO2019/105881
PCT Pub. Date: Jun. 6, 2019

(65) Prior Publication Data
US 2021/0179541 A1     Jun. 17, 2021

(30) Foreign Application Priority Data
Dec. 1, 2017   (EP) .................................... 17204842

(51) Int. Cl.
| C07C 233/88 | (2006.01) |
| C07C 51/09 | (2006.01) |
| C07C 227/18 | (2006.01) |
| C07C 231/02 | (2006.01) |
| C07C 231/12 | (2006.01) |

(52) U.S. Cl.
CPC ............ *C07C 233/88* (2013.01); *C07C 51/09* (2013.01); *C07C 227/18* (2013.01); *C07C 231/02* (2013.01); *C07C 231/12* (2013.01); *C07B 2200/13* (2013.01)

(58) Field of Classification Search
None
See application file for complete search history.

(56) References Cited

FOREIGN PATENT DOCUMENTS

| GB | 2179941 A | 10/1986 |
| WO | 2000/06568 A1 | 2/2000 |
| WO | 2000/006569 A1 | 2/2000 |
| WO | 2002/042301 A1 | 5/2002 |
| WO | 2003/095451 A1 | 11/2003 |
| WO | 2007057643 | 5/2007 |
| WO | 2011/147809 A1 | 1/2011 |
| WO | 2011/051165 A1 | 5/2011 |
| WO | 2012/004258 A1 | 1/2012 |
| WO | 2012/028647 A1 | 3/2012 |
| WO | 2012/059549 A1 | 5/2012 |
| WO | 2012139888 A1 | 10/2012 |

OTHER PUBLICATIONS

Gerlach, A. et al., "Industrial Application of Chiral Bisphosphines," Specialty Chemicals Magazine, Apr. 2004, pp. 37-38.
Montani, D. et al., "Updated Clinical Classification of Pulmonary Hypertension," in Pulmonary Circulation: Diseases and their Treatment, Third Edition, Peacock, A. J. et al. (Eds ), 2011, Hodder Arnold Publ., pp. 197-206.
Hoeper, M.M. et al. Journal of the American College of Cardiology, vol. 54, No. 1, 2009, pp. S85-S96.
Leggio, A. et al., "One-pot Synthesis of Amides from Carboxylic Acids Activated Using Thionyl Chloride", RSC Advances, 2016, 6, 34468-34475.
International Search Report and Written Opinion of PCT/EP2018/082526, dated Jun. 6, 2019.

*Primary Examiner* — Sudhakar Katakam
*Assistant Examiner* — Jennifer C Sawyer
(74) *Attorney, Agent, or Firm* — Quarles & Brady LLP

(57) ABSTRACT

The present invention relates to a novel and improved process for preparing (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (I), to the compound of the formula (I) in crystalline form and to their use for the treatment and/or prevention of diseases, in particular for the treatment and/or prevention of cardiovascular, cardiopulmonary and cardiorenal disorders.

1 Claim, 3 Drawing Sheets

Figure 1:
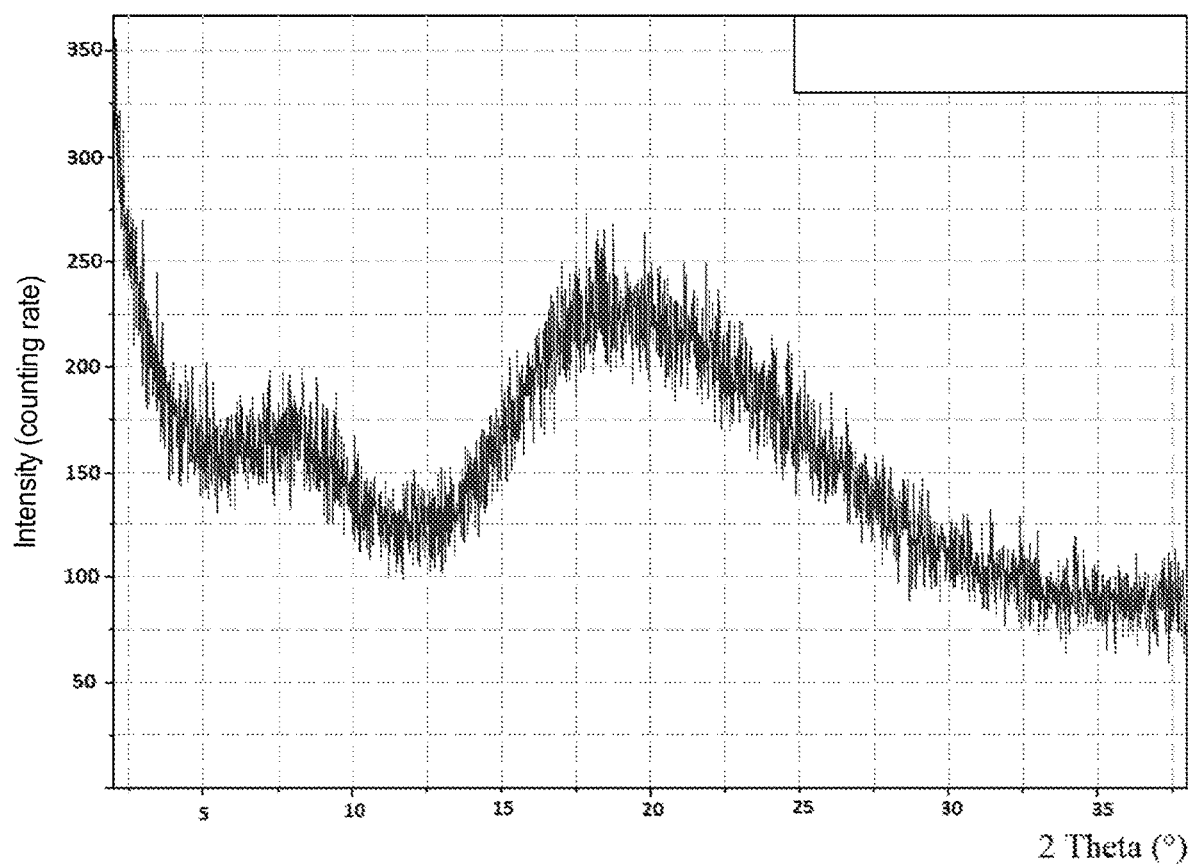

METHOD FOR PRODUCING (3S)-3-(4-CHLORO-3-{[(2S,3R)-2-(4-CHLOROPHENYL)-4,4,4-TRIFLUORO-3-METHYLBUTANOYL]AMINO}PHENYL)-3-CYCLO-PROPYLPROPANOIC ACID AND THE CRYSTALLINE FORM THEREOF FOR USE AS A PHARMACEUTICAL INGREDIENT

This application is a national stage entry under 35 U.S.C. § 371 for International Application No. PCT/EP2018/082526, filed Nov. 26, 2018, the contents of which are incorporated herein by reference in its entirety, which claims priority to European Patent Application No. 17204842.3, filed Dec. 1, 2017.

The present invention relates to a novel and improved process for preparing (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (I)

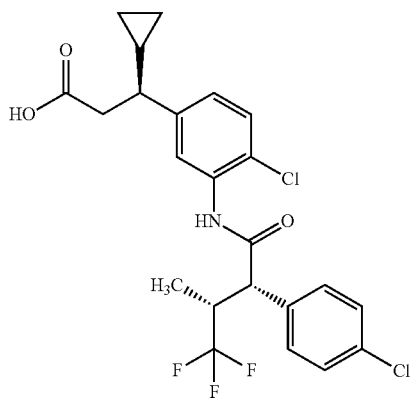

in particular of the compound of formula (I) in crystalline modification 1 (I-1), and to its use for the treatment and/or prevention of diseases, in particular for the treatment and/or prevention of cardiovascular, cardiopulmonary and cardio-renal disorders.

In the context of this invention, (I-A) refers to the compound of the formula (I) in amorphous form; the crystalline modification 1 is referred to as (I-1). Without further differentiation, the compound of the formula (I) is present in one or more modifications or as a solvate.

The compound of the formula (I) and the compound of the formula (I) in crystalline modification 1 (I-1) act as activators of soluble guanylate cyclase and can be employed as agents for the prophylaxis and/or treatment of cardiovascular disorders and in particular renal disorders, for example for the treatment of chronic kidney disease (CKD).

The compound of the formula (I) in amorphous form (I-A) and its preparation process are described in the patent application WO 2012/139888. The synthesis described therein has the disadvantage that this synthesis is unsuitable for a large industrial scale process as it requires a large number of chromatographic purification steps, inter alia. These are generally technically highly complex, cost-intensive and require a large solvent consumption, and should therefore be avoided, if possible. Some stages are not achievable on an industrial scale due to safety and process technology difficulties. In addition, in relation to the volume of a batch, only little product can be produced.

There was therefore a need for a synthesis practicable on a large industrial scale that affords the compound of the crystalline modification 1 (I-1) reproducibly in a high overall yield, with low production costs and high purity and meets all regulatory requirements.

The compound (I-A) and its preparation process are known in principle. WO 2012/139888 discloses the preparation of the compound (I-A) starting from the compound of the formula (II) and the tert-butyl ester (III-A) by amide coupling and subsequent ester hydrolysis in two steps. The compound of the formula (I) was obtained as an amorphous solid by concentration of chromatography fractions. A defined process for the crystallization of the final stage for adjusting polymorphism has hitherto not been described.

The following scheme 1 shows the known process for preparing the compound (I-A).

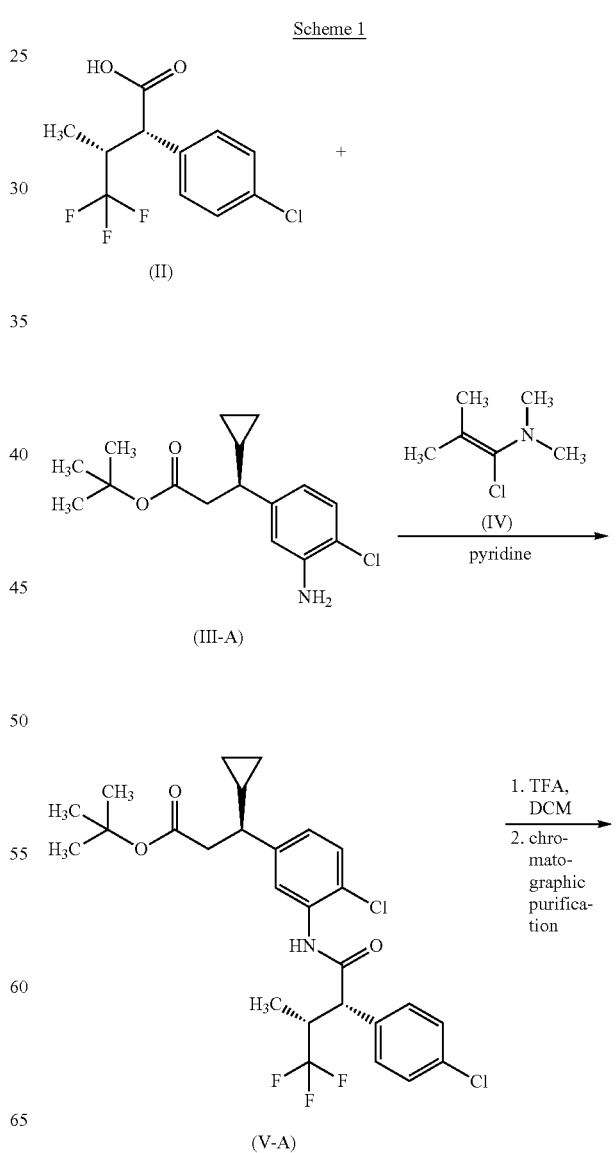

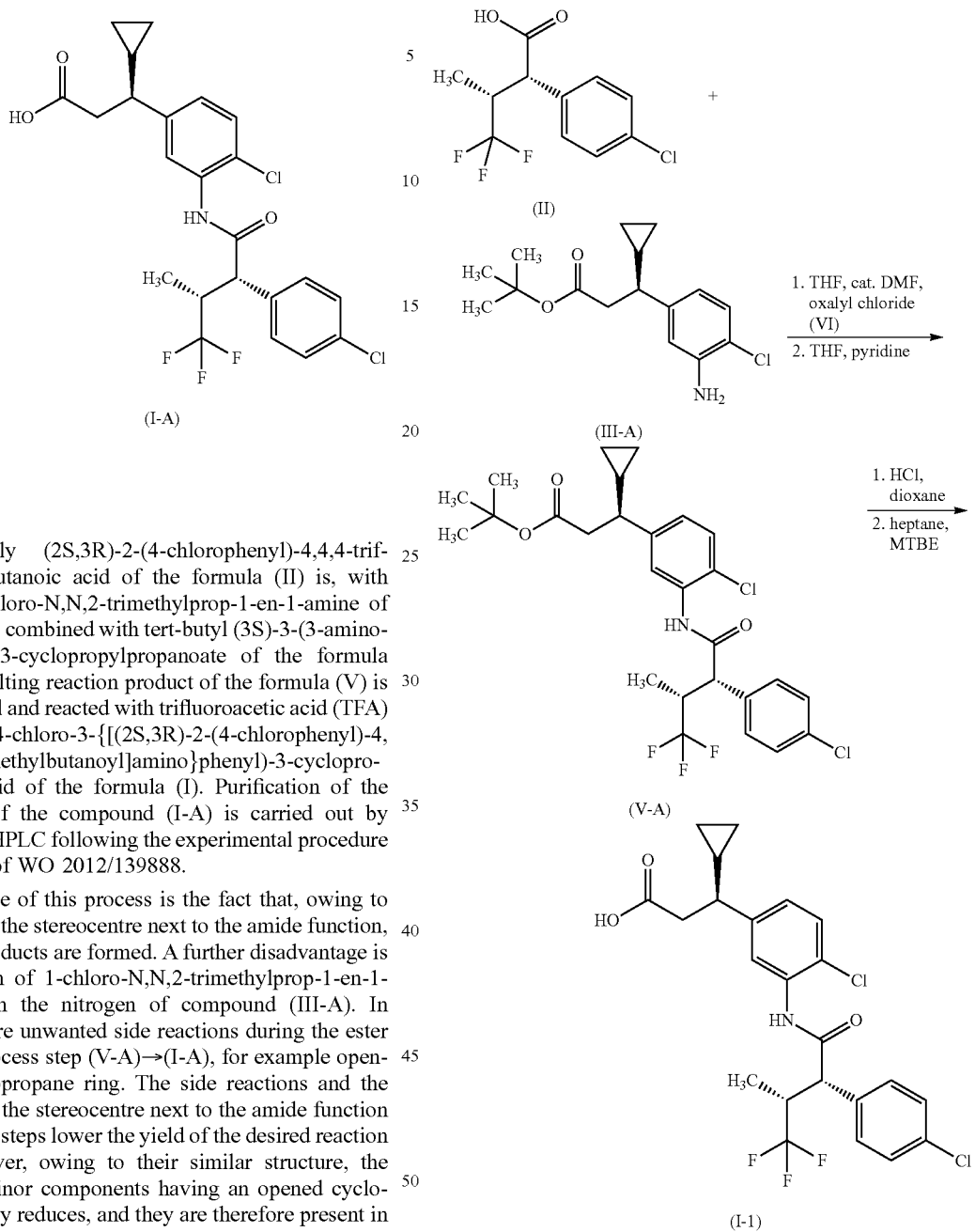

Here, initially (2S,3R)-2-(4-chlorophenyl)-4,4,4-trifluoro-3-methylbutanoic acid of the formula (II) is, with addition of 1-chloro-N,N,2-trimethylprop-1-en-1-amine of the formula (IV), combined with tert-butyl (3S)-3-(3-amino-4-chlorophenyl)-3-cyclopropylpropanoate of the formula (III-A). The resulting reaction product of the formula (V) is obtained as an oil and reacted with trifluoroacetic acid (TFA) to give (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (I). Purification of the crude product of the compound (I-A) is carried out by preparative RP-HPLC following the experimental procedure of Example 22 of WO 2012/139888.

A disadvantage of this process is the fact that, owing to epimerization of the stereocentre next to the amide function, unwanted by-products are formed. A further disadvantage is the side reaction of 1-chloro-N,N,2-trimethylprop-1-en-1-amine (IV) with the nitrogen of compound (III-A). In addition, there are unwanted side reactions during the ester hydrolysis in process step (V-A)→(I-A), for example opening of the cyclopropane ring. The side reactions and the epimerization of the stereocentre next to the amide function during these two steps lower the yield of the desired reaction product. Moreover, owing to their similar structure, the proportion of minor components having an opened cyclopropyl ring hardly reduces, and they are therefore present in the active compound and have to be removed by highly complex chromatographic purification.

This complex purification method involves the use of expensive chiral phases, large amounts of solvent and high expenditure for apparatuses and is thus ill-suited for producing compound (I-A) on a large scale.

A further disadvantage is the equimolar use of the compound of the formula (IV) which, owing to its carcinogenic properties, represents a considerable safety risk for man and environment, in particular when working on a large industrial scale. The process has to be adapted to these risks via increased safety expenditure.

Scheme 2 below illustrates the reaction steps of the process according to the invention in an exemplary manner.

For process step (II)+(III-A)→(V-A), (2S,3R)-2-(4-chlorophenyl)-4,4,4-trifluoro-3-methylbutanoic acid of the formula (II) is initially charged in a solvent. Suitable solvents are aprotic polar solvents, for example THF (tetrahydrofuran), DCM (dichloromethane), dioxane, toluene, DMF (dimethylformamide), NMP (N-methyl-2-pyrrolidone), DMA (dimethylacetamide) or ether. Preference is given to using THF. Preferably, a catalytic amount of DMF is added to the solvent. The carboxylic acid of the formula (II) is then converted into the corresponding carbonyl chloride or mixed carboxylic anhydride. The carbonyl chloride is produced in a customary manner by treating the carboxylic acid with thionyl chloride or oxalyl chloride. Preference is given to using 0.5 eq to 2 eq of oxalyl chloride, particularly preferably 1.1 eq of oxalyl chloride. The mixed carboxylic anhydride is prepared in a customary manner by treating the carboxylic acid with suitable sulfonyl chlorides. Preference is given to using methanesulfonyl chloride. The reaction is carried out at from 0° C. to 50° C., preferably from 0° C. to 25° C., particularly preferably at 20° C. The reaction takes place in the absence of a base.

In a second reaction apparatus, tert-butyl (3S)-3-(3-amino-4-chlorophenyl)-3-cyclopropylpropanoate of the formula (III-A) is dissolved in a solvent and an amine base. For protecting the acid function, instead of the tert-butyl ester of the compound of the formula (III-A), use may also be made of other esters known to the person skilled in the art, for example methyl, ethyl, propyl, isopropyl, butyl, sec-butyl or isobutyl esters. Preference is given to using tert-butyl ester. Suitable solvents are aprotic polar solvents, for example THF, DCM, dioxane, toluene, DMF, NMP, DMA or ether; preference is given to using THF. Suitable amine bases are triethylamine, N-methylmorpholine, N-methylpiperidine, N,N-diisopropylethylamine, pyridine, 4-N,N-dimethylaminopyridine, 1,8-diazabicyclo[5.4.0]undec-7-ene (DBU) or 1,5-diazabicyclo[4.3.0]non-5-ene (DBN). Preference is given to using 5 eq to 15 eq of pyridine, particularly preferably 10 eq of pyridine. To this solution, the acid chloride or the mixed carboxylic anhydride intermediate is added at from 0° C. to 50° C., preferably from 0° C. to 25° C., particularly preferably at 20° C. Coupling with formation of the compound of the formula (V-A) proceeds rapidly (1 h), very clean and without epimerization. Following aqueous work-up with citric acid, the solvent is evaporated and the solid is dissolved in a mixture of MTBE and heptane in a volume ratio of 1:1 to 1:8, preferably 1:4. The reaction solution is concentrated to half of its volume and slowly cooled to room temperature and the compound of the formula (V-A) is obtained as a crystalline solid in very high purity and good yield. After crystallization, the compound of the formula (V-A) is obtained in a yield of 86% in high purity.

The compound of the formula (V-A) is dissolved in dioxane and, by addition of HCl, converted into the compound of the formula (I). Preferably, the compound of the formula (I) is converted into formula (I-1) using the following crystallization process: The compound of the formula (I), present in one or more modifications or as a solvate, is stirred in an inert solvent, preferably selected from a list comprising heptane, 2-methoxy-2-methylpropane, ethanol, ethyl acetate or mixtures of these solvents, at a temperature of from 20° C. to 120° C., preferably from 30° C. to 100° C., particularly preferably from 40° C. to 60° C., and the compound (I-1) is isolated, optionally after cooling.

Preferred inert solvents for the process for preparing the compound (I-1) are heptane, mixtures of ethanol and water in a volume ratio of 1:4, mixtures of 2-methoxy-2-methylpropane and heptane in a volume ratio of from 4:1 to 1:25 and mixtures of ethyl acetate and heptane, where the proportion of ethyl acetate is 2% or less.

Particularly preferred inert solvents are mixtures of 2-methoxy-2-methylpropane and heptane in a volume ratio of from 1:1 to 4:1, very particularly preferably 2.3:1, which in a subsequent step are, by addition of heptane, adjusted to a volume ratio of from 1:13 to 1:25, very particularly preferably 1:18.

For better crystallization, the solution may be seeded with compound (I-1). For seeding, compound (I-1) may be obtained, for example, from compound (I-A) by stirring in n-heptane or a mixture of ethanol and water in a ratio of 1:4, preferably at 25° C.

Compared to the prior art (WO 2012/139888, Example 99A), the novel synthesis has the advantage that the base-free conversion of the compound of the formula (II) into the corresponding carbonyl chloride or carboxylic anhydride surprisingly does not lead to the epimerization of the stereocentre next to the amide function. Nor is epimerization observed in the next process step (II)+(III-A)→(V-A). Accordingly, the coupling reaction proceeds with a high yield of the compound of the formula (V-A) of 86% of theory and with high purity. If the reaction (II)+(III-A)→(V-A) is employed on an industrial scale, a yield of about 70% and additionally 5% contamination of the product by the side reaction of the 1-chloro-N,N2-trimethylprop-1-en-1-amine of the formula (IV) with the nitrogen of compound (III-A) are obtained.

In addition, the equimolar use of the carcinogenic compound 1-chloro-N,N,2-trimethylprop-1-en1 amine (IV) is dispensed with. Accordingly, by-product formation by reaction of the compound of the formula (III-A) with the compound of the formula (IV) is not possible.

Using hydrochloric acid (HCl) and dioxane instead of trifluoroacetic acid (TFA) and dichloromethane (DCM) in process step (V-A)→(I-A), surprisingly, fewer by-products are formed. These by-products formed in the process according to WO 2012/139888 have an opened cyclopropyl ring and, owing to their similar structure, their proportion hardly reduces. They are therefore present in the active compound or have to be removed by a very complex chromatographic purification.

Surprisingly, it has been found that the compound (I-1) in the crystallization process described crystallizes in high yield and purity. Thus, complex chromatography can be dispensed with and (3<S)-3-(4-chloro-3-{[(2S,3R)-2-(4-chlorophenyl)-4,4,4-trifluoro-3-methylbutanol] amino}phenyl)-3-cyclopropylpropanoic acid is, in contrast to the prior art (WO 2012/139888), not formed in amorphous form but in the crystalline form of modification 1 (I-1) in a high yield of 88% of theory, and additionally in high purity.

The present invention provides a process for preparing the compound of the formula (V)

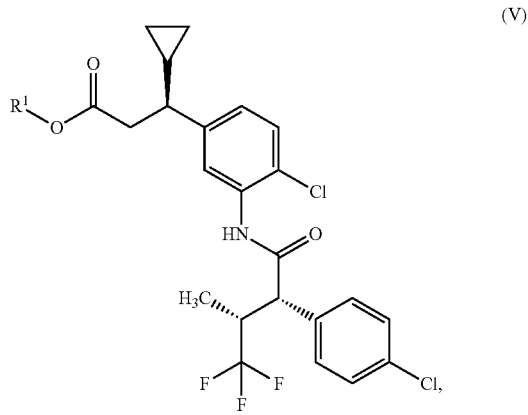

(V)

in which R¹ represents (C₁-C₄)-alkyl,
characterized in that the compound of the formula (II)

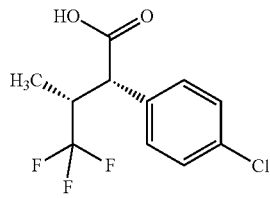
(II)

is reacted under base-free conditions with a compound of the formula (III)

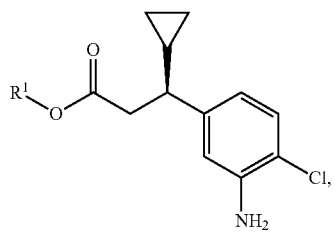
(III)

in which R¹ represents (C₁-C₄)-alkyl.

The present invention further provides a process for preparing the compound of the formula (V)
in which R¹ represents (C₁-C₄)-alkyl,
characterized in that the compound of the formula (II)

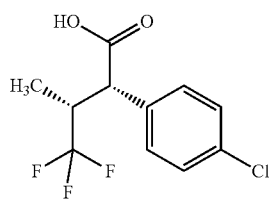
(II)

is reacted under base-free conditions to give the corresponding carbonyl chloride intermediate or the corresponding carboxylic anhydride intermediate and reacted in a coupling reaction with the compound of the formula (III)

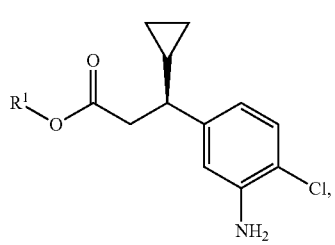
(III)

in which R¹ represents (C₁-C₄)-alkyl.

The present invention further provides a process for preparing the compound of the formula (V)
in which
R¹ represents (C₁-C₄)-alkyl,
characterized in that the compound of the formula (II)

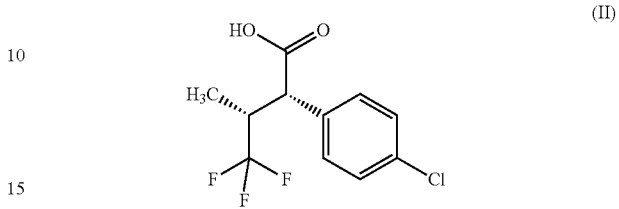
(II)

is reacted under base-free conditions with a compound of the formula (VI)

(VI)

which is reacted in a reaction with the compound of the formula (III)

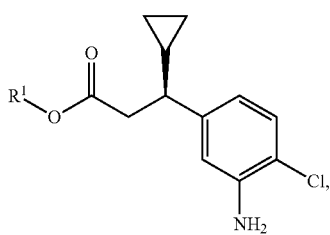
(III)

in which R¹ represents (C₁-C₄)-alkyl.

The present invention further provides a process for preparing the compound of the formula (V) using, instead of the compound of the formula (VI), the compound of the formula (VI-A)

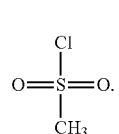
(VI-A)

A preferred subject of the present invention is the process for preparing the compound of the formula (V) using catalytic amounts of DMF for the synthesis of the carbonyl chloride intermediate.

A preferred subject of the present invention is the process for preparing the compound of the formula (V) using catalytic amounts of DMF for the synthesis of the carboxylic anhydride intermediate.

A preferred subject of the present invention is the process for preparing the compound of the formula (V) at a temperature of from 0° C. to 50° C., preferably from 0° C. to 25° C., particularly preferably 20° C.

The present invention further provides a process for preparing the compound of the formula (I), characterized in that the compound of the formula (V)

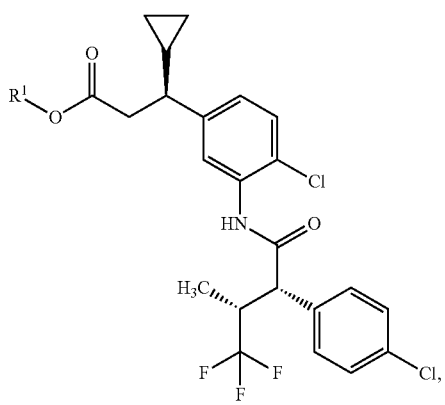

(V)

in which $R^1$ represents $(C_1-C_4)$-alkyl,
is reacted in the presence of dioxane and hydrochloric acid to give the compound of the formula (I).

The present invention provides a process for preparing the compound of the formula (I), characterized in that the compound of the formula (II)

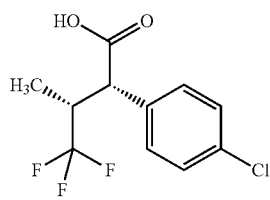

(II)

is reacted under base-free conditions with the compound of the formula (III)

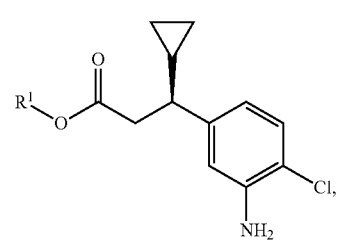

(III)

in which $R^1$ represents $(C_1-C_4)$-alkyl,
to give the compound of the formula (V)

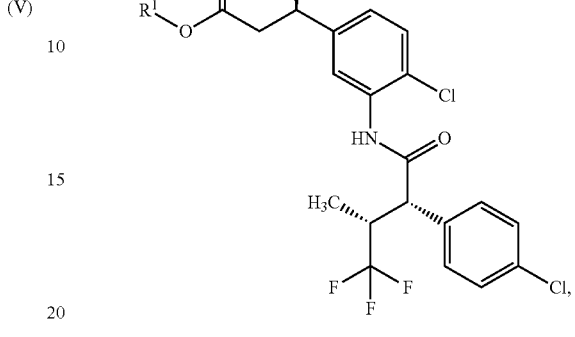

(V)

in which $R^1$ represents $(C_1-C_4)$-alkyl,
and in a subsequent step reacted in the presence of dioxane and hydrochloric acid to give the compound of the formula (I).

The present invention provides a process for preparing the compound of the formula (I), characterized in that the compound of the formula (II)

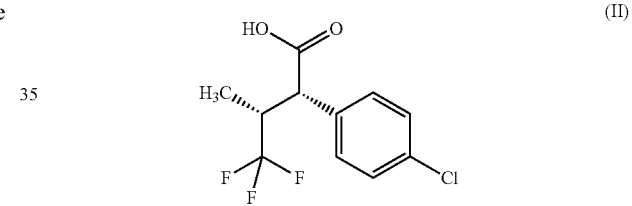

(II)

is reacted under base-free conditions with a compound of the formula (VI)

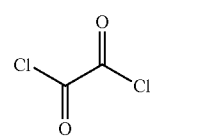

(VI)

which is reacted in a reaction with the compound of the formula (III)

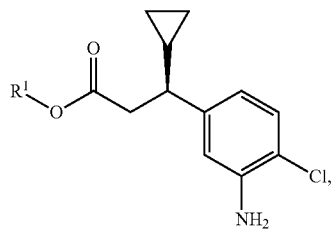

(III)

in which R¹ represents (C₁-C₄)-alkyl,
to give the compound of the formula (V)

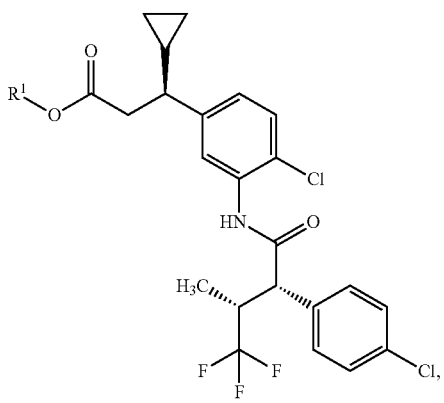

in which
R¹ is (C₁-C₄)-alkyl,
and in a subsequent step reacted in the presence of dioxane and hydrochloric acid to give the compound of the formula (I).

A preferred subject of the present invention is the process for preparing the compound of the formula (I) using catalytic amounts of DMF for the synthesis of the carbonyl chloride intermediate.

A preferred subject of the present invention is the process for preparing the compound of the formula (I) using catalytic amounts of DMF for the synthesis of the carboxylic anhydride intermediate.

A preferred subject of the present invention is the process for preparing the compound of the formula (I) at a temperature of from 0° C. to 50° C., preferably from 0° C. to 25° C., particularly preferably 20° C.

The present invention further provides the compound of the formula (I) in crystalline form of modification 1 (I-1)

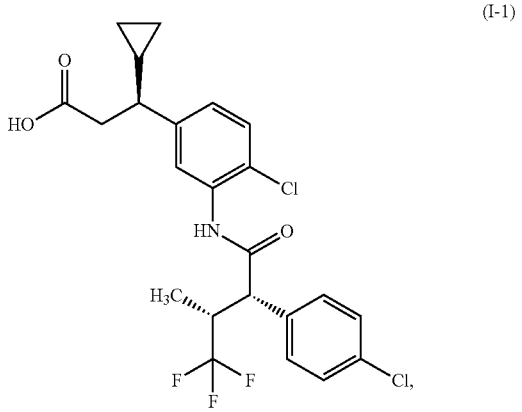 [SMILES: C[C@H]([C@H](C(=O)Nc1cc([C@@H](CC(=O)O)C2CC2)ccc1Cl)c1ccc(Cl)cc1)C(F)(F)F]

characterized in that the IR spectrum of the compound exhibits band maxima at 1709, 1660, 1534, 1491, 1263, 1167, 1131, 1093, 1016 cm⁻¹.

The present invention further provides the compound of the formula (I) in crystalline form of modification 1 (I-1)

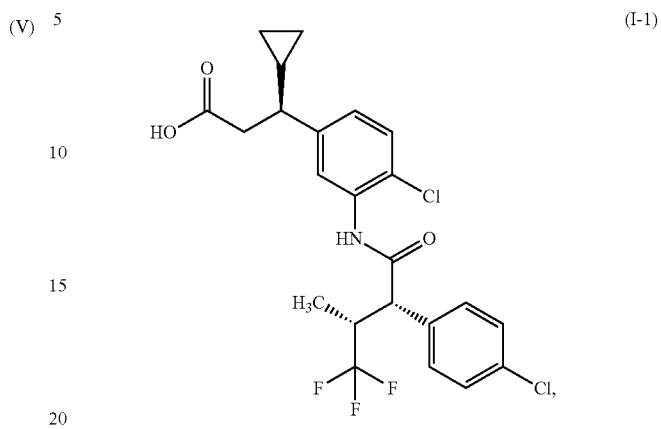

characterized in that the x-ray diffractogram of the compound exhibits peak maxima of the 2 theta angle at 7.0, 8.2, 11.1, 14.7, 17.2, 17.5, 18.7, 19.8.

The present invention further provides a process for preparing the compound (I-1), characterized in that the compound of the formula (I), present in one or more modifications or as a solvate, is stirred in an inert solvent selected from a list comprising heptane, 2-methoxy-2-methylpropane, ethanol, ethyl acetate or mixtures of these solvents, at a temperature of from 20° C. to 120° C., preferably from 30° C. to 100° C., particularly preferably from 40° C. to 60° C., and the compound (I-1) is isolated, optionally after cooling.

Preferred inert solvents for the process for preparing the compound (I-1) are heptane, mixtures of ethanol and water in a volume ratio of 1:4, mixtures of 2-methoxy-2-methylpropane and heptane in a volume ratio of from 4:1 to 1:25 and mixtures of ethyl acetate and heptane, where the proportion of ethyl acetate is 2% or less.

Particularly preferred inert solvents are mixtures of 2-methoxy-2-methylpropane and heptane in a volume ratio of from 1:1 to 4:1, very particularly preferably 2.3:1, which in a subsequent step are, by addition of heptane, adjusted to a volume ratio of from 1:13 to 1:25, very particularly preferably 1:18.

In an alternative process according to the invention for preparing the compound (I-1), instead of the tert-butyl ester of the formula (III) the corresponding free acid of the formula (VI) is used. Scheme 3 below illustrates the reaction steps of the process according to the invention in an exemplary manner.

Scheme 3

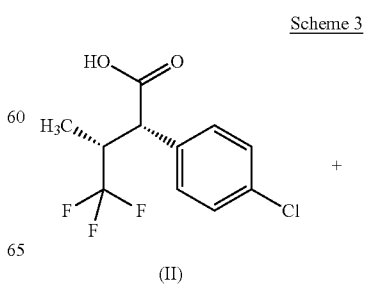

+

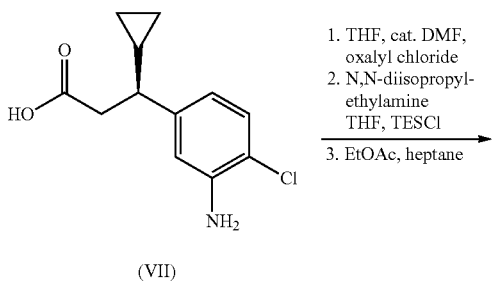

[THF, tetrahydrofuran, TESCl, chlorotriethylsilane; EtOAc, ethyl acetate]

Hereinbelow, the alternative process according to the invention for preparing the compound (I-1) is described in detail.

For process step (II)+(VII)→(I-1), (2S,3R)-2-(4-chlorophenyl)-4,4,4-trifluoro-3-methylbutanoic acid of the formula (II) is initially charged in a solvent. Suitable solvents are aprotic polar solvents, for example THF, DCM, dioxane, toluene, DMF, NMP, DMA or ether; preference is given to using THF. Preferably, a catalytic amount of DMF is added to the solvent. The carboxylic acid of the formula (II) is then converted into the corresponding carbonyl chloride or mixed carboxylic anhydride. The carbonyl chloride is produced in a customary manner by treating the carboxylic acid with thionyl chloride or oxalyl chloride; preference is given to using oxalyl chloride, particularly preferably 1.1 eq of oxalyl chloride. The mixed carboxylic anhydride is prepared in a customary manner by treating the carboxylic acid with suitable sulfonyl chlorides; preference is given to using methanesulfonyl chloride. The reaction is carried out at from 0° C. to 50° C., preferably from 0° C. to 25° C. The reaction takes place in the absence of a base.

In a second reaction apparatus, (3S)-3-(3-amino-4-chlorophenyl)-3-cyclopropylpropanoic acid (VII) or a salt of this compound is dissolved in an aprotic, polar solvent and an amine base. Suitable for use as aprotic polar solvent is, for example, THF, DCM, dioxane, toluene, DMF, NMP, DMA or ether; preference is given to using THF. Suitable amine bases are, for example, triethylamine, N-methylmorpholine, N-methylpiperidine, N,N-diisopropylethylamine, pyridine, 4-N,N-dimethylaminopyridine, 1,8-diazabicyclo[5.4.0]undec-7-ene (DBU) or 1,5-diazabicyclo[4.3.0]non-5-ene (DBN); preference is given to using N,N-diisopropylethylamine, particularly preferably 5 eq of N,N-diisopropylethylamine. To allow selective coupling of the carboxylic acid (II) to the amine function of the compound of the formula (VII), the carboxylic acid moiety of the compound of the formula (VII) has to be protected. To this end, the carboxylic acid moiety of the compound of the formula (VII) is, preferably at from 0° C. to 50° C., particularly preferably at 20° C., protected with a silyl protective group in the presence of an aprotic, polar solvent and an amine base. Suitable for use as organosilicon compound for forming a silyl protective group are organosilicon compounds known to the person skilled in the art, for example chlorotriethylsilane (Tesco), chlorotrimethylsilane or tert-butyl(chloro)dimethylsilane; preference is given to using chlorotriethylsilane (TESCl). The carbonyl chloride or carboxylic anhydride corresponding to the compound of the formula (II) is added to this reaction solution. The silyl group is removed by aqueous, acidic work-up.

Furthermore, it was surprisingly found that the compound (I-1) can be purified in heptane and EtOAc, which replaces complex chromatography. In this crystallization process, the EtOAc-containing solution of the crude product is redistilled to heptane. To this end, heptane is added and solvent is distilled off at a temperature of from 40° C. to reflux temperature, preferably 55° C. After renewed addition of heptane, a small amount of crystalline product is added (seeding) and the mixture is cooled so that the compound (I-1) can be isolated. In this manner, complex chromatography can be dispensed with and the product is, in contrast to the prior art (WO 2012/139888), formed in crystalline form in a high yield of 88% of theory and high purity. In the reaction, EtOAc acts as solubilizer and may be present in small amounts even after redistillation.

Compared to the prior art (WO 2012/139888, Example 99A), the novel synthesis has the advantage that the base-free conversion of the compound of the formula (II) into the corresponding carbonyl chloride or carboxylic anhydride surprisingly does not lead to the epimerization of the stereocentre next to the amide function. During the coupling reaction, epimerization is likewise not observed. The way the reaction is conducted, compound (I-1) is prepared in a one-step process from the starting materials for the coupling. Compared to the prior art, the isolation of a solid is not required. Since there is no additional ester hydrolysis in the process (II)+(VII)→(I-1), there is no formation of disadvantageous by-products having an opened cyclopropyl ring which have to be removed by complex chromatographic purification and simultaneously result in a lower yield.

It is a further advantage that the compound of the formula (VII) can be obtained by racemate resolution. The racemate resolution is shown in Scheme 8 and is markedly more efficient than separation of the enantiomers via chiral chromatography, which is required for separating the enantiomers of the compound of the formula (III).

In addition, the equimolar use of the carcinogenic compound 1-chloro-N,N,2-trimethylprop-1-en-1 amine of the formula (IV) can be dispensed with. Accordingly, the disadvantageous by-product formation by reaction of the compound of the formula (III) with the compound of the formula (IV) is not possible.

The present invention furthermore provides a process for preparing the compound of the formula (I), characterized in that the compound of the formula (II)

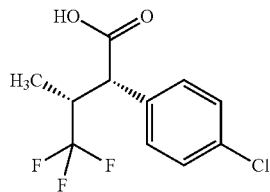
(II)

is reacted under base-free conditions with the compound of the formula (VII-A)

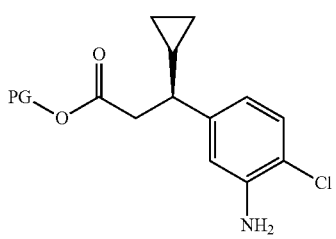
(VII-A)

in which
PG represents a silyl protective group,
and with removal of the silyl protective group in aqueous acidic solution converted into the compound of the formula (I)

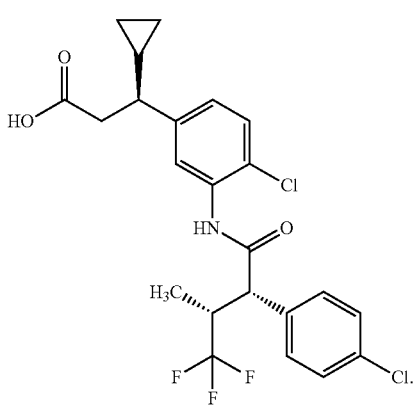
(I)

The present invention furthermore provides a process for preparing the compound of the formula (I), characterized in that the compound of the formula (II)

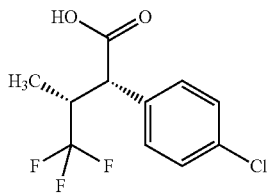
(II)

is reacted under base-free conditions to give the corresponding carbonyl chloride intermediate or the corresponding carboxylic anhydride intermediate and reacted with the compound of the formula (VII-A)

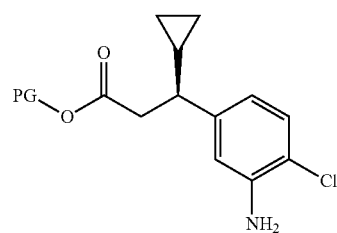
(VII-A)

in which
PG represents a silyl protective group,
and with removal of the silyl protective group in aqueous acidic solution converted into the compound of the formula (I)

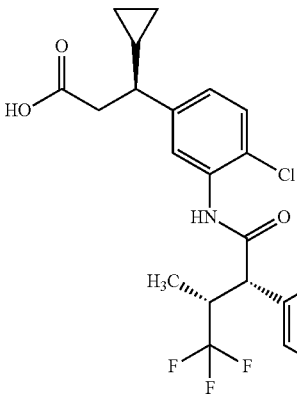
(I)

The present invention preferably provides a process for preparing the compound of the formula (I), characterized in that the compound of the formula (II)

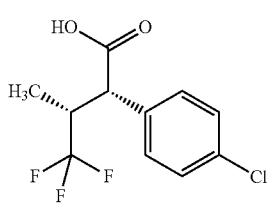
(II)

is reacted under base-free conditions with a compound of the formula (VI)

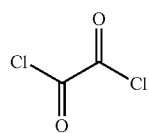
(VI)

which is converted in a reaction with the compound of the formula (VII-A)

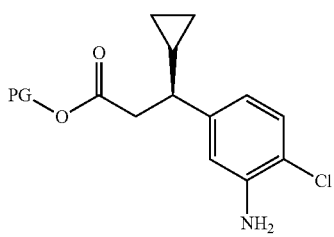
(VII-A)

in which
PG represents chlorotriethylsilyl,
and with removal of the silyl protective group in aqueous acidic solution converted into the compound of the formula (I)

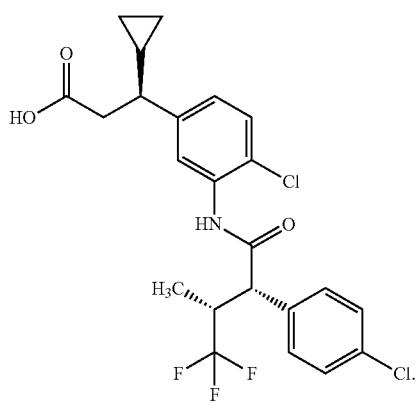
(I)

The present invention furthermore provides a process for preparing the compound of the formula (I), characterized in that the compound of the formula (II)

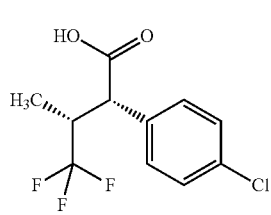
(II)

is, under base-free conditions and using an organosilicon compound, preferably chlorotriethylsilane (TESCl), chlorotrimethylsilane or tert-butyl(chloro)dimethylsilane, particularly preferably chlorotriethylsilane (TESCl), reacted with the compound of the formula (VII),

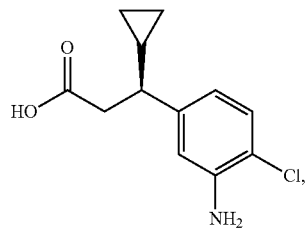
(VII)

or a salt of this compound,
and with removal of the silyl protective group, preferably in aqueous acidic solution converted into the compound of the formula (I)

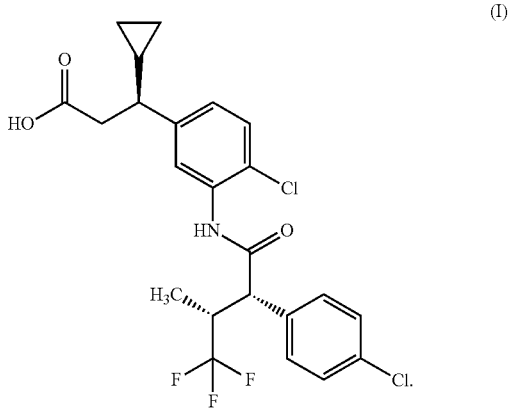 [SMILES: C[C@H]([C@H](C(=O)Nc1cc([C@@H](CC(=O)O)C2CC2)ccc1Cl)c1ccc(Cl)cc1)C(F)(F)F]
(I)

The present invention furthermore provides a process for preparing the compound of the formula (I), characterized in that the compound of the formula (II)

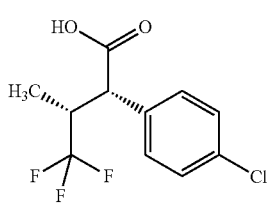
(II)

is, under base-free conditions, converted into the corresponding carbonyl chloride intermediate or the corresponding carboxylic anhydride intermediate and, using an organosilicon compound, preferably chlorotriethylsilane (TESCl), chlorotrimethylsilane or tert-butyl(chloro)dimethylsilane, particularly preferably chlorotriethylsilane (TESCl), reacted with the compound of the formula (VII),

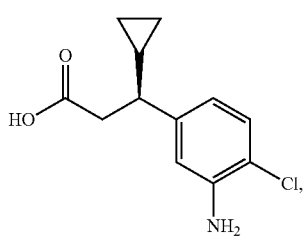

(VII)

or a salt of this compound,
and with removal of the silyl protective group in aqueous acidic solution converted into the compound of the formula (I)

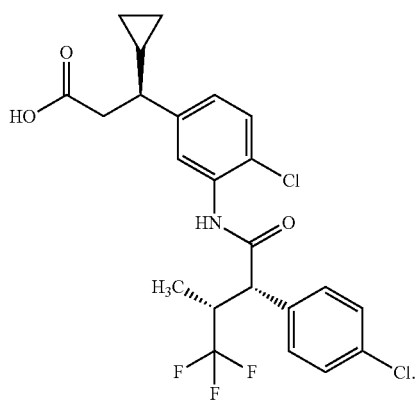

(I)

The present invention preferably provides a process for preparing the compound of the formula (I), characterized in that the compound of the formula (II)

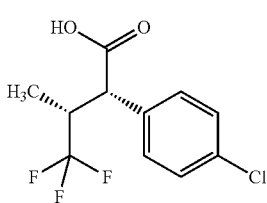

(II)

is reacted under base-free conditions with a compound of the formula (VI)

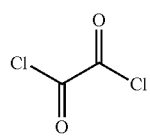

(VI)

which, using an organosilicon compound, preferably chlorotriethylsilane (TESCl), chlorotrimethylsilane or tert-butyl(chloro)dimethylsilane, particularly preferably chlorotriethylsilane (TESCl), is converted in a reaction with the compound of the formula (VII),

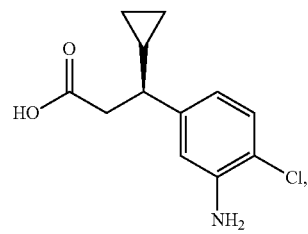

(VII)

or a salt of this compound,
with removal of the silyl protective group in aqueous acidic solution into the compound of the formula (I)

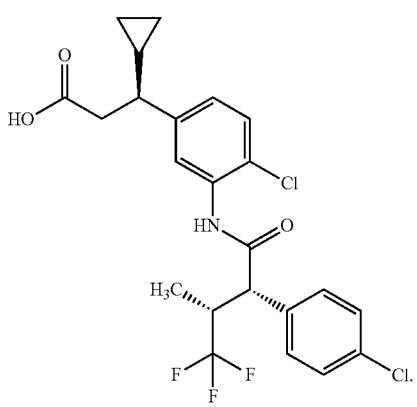

(I)

A preferred subject of the present invention is the process for preparing the compound of the formula (I) using catalytic amounts of DMF for the synthesis of the carbonyl chloride intermediate.

A preferred subject of the present invention is the process for preparing the compound of the formula (I) using catalytic amounts of DMF for the synthesis of the carboxylic anhydride intermediate.

A further subject of the present invention is a process for preparing the compound (I-1), characterized in that the compound of the formula (I), present in one or more modifications or as a solvate, is dissolved in ethyl acetate and the compound (I-1) is isolated after redistillation to heptane and optionally after cooling.

A further subject of the present invention is the preparation of (2S,3R)-2-(4-chlorophenyl)-4,4,4-trifluoro-3-methylbutanoic acid of the formula (II), which serves as starting material for the preparation of the compound of the formula (I). The preparation of the compound of the formula (II) is known in principle. WO 2012/139888 discloses the preparation of the compound of the formula (II) starting from the compounds of the formula (VIII) and (IX) in eight steps.

The following Scheme 4 shows the known process for preparing the compound of the formula (II).

Scheme 4

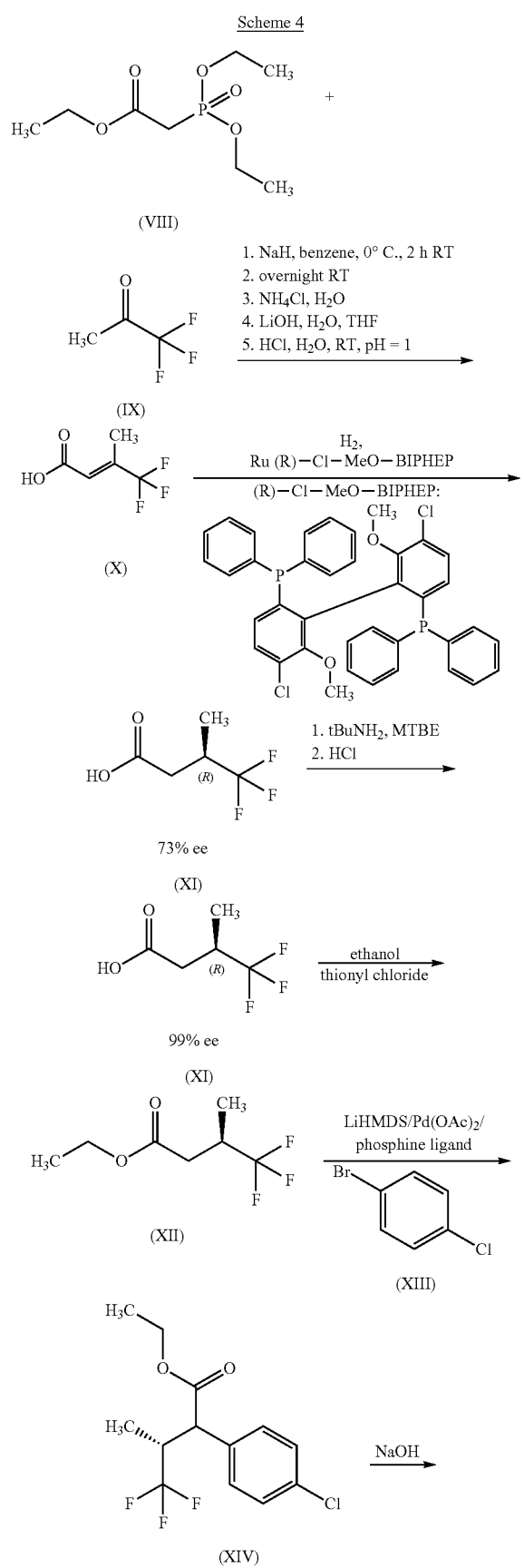

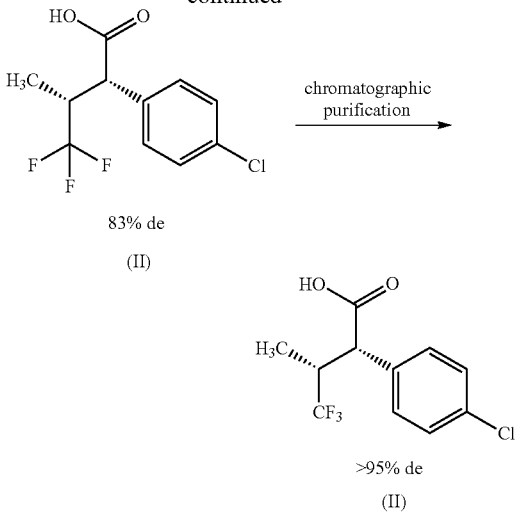

83% de (II)

>95% de (II)

Here, ethyl (diethoxyphosphoryl)acetate of the formula (VIII) is, in benzene at 0° C., deprotonated with sodium hydride and converted with trifluoroacetone (IX) into the corresponding ester of the compound ethyl 4,4,4-trifluoro-3-methyl-2-butenoate of the formula (X). This is hydrolyzed with lithium hydroxide in a mixture of THF and water to give the acid which, after acidification with hydrochloric acid to pH=1, is obtained in a yield of 40%. Subsequently, by hydrogenation with (S)—Cl-MeO-BIPHEP[ruthenium (1S)-5,5'-dichloro-6,6'-dimethoxy[1,1'-biphenyl]-2,2'-diyl] bis[diphenylphosphine], (3R)-4,4,4-trifluoro-3-methylbutanoic acid of the formula (XI) is obtained.

(3R)-4,4,4-Trifluoro-3-methylbutanoic acid of the formula (XI) is reacted with thionyl chloride using ethanol as solvent. The resulting compound of the formula (XII) is isolated, dissolved in toluene and, under an atmosphere of argon, added to a solution of lithium hexamethyldisilazide in toluene, with care being taken not to exceed a temperature of −10° C. (Solution A). Under an atmosphere of argon and at room temperature, 1-bromo-4-chlorobenzene of the formula (XIII) is dissolved in toluene, and palladium(II) acetate and 2-dicyclohexyl phosphino-2'-(N,N-dimethylamino)biphenyl are added (Solution B). When Solutions A and B are combined, ethyl (3R)-2-(4-chlorophenyl)-4,4,4-trifluoro-3-methylbutanoate of the formula (XIV) is formed. The ethyl ester of the compound of the formula (XIV) is hydrolyzed by reaction with aqueous sodium hydroxide solution, giving (+)-(2S,3R)-2-(4-chlorophenyl)-4,4,4-trifluoro-3-methylbutanoic acid of the formula (II). By subsequent chromatographic purification, a diastereomer purity of >95% is achieved.

A disadvantage of the process for preparing (+)-(2S,3R)-2-(4-chlorophenyl)-4,4,4-trifluoro-3-methylbutanoic acid of the formula (II) is the use of the solid sodium hydride in the reaction step (VIII)+(IX)→(X). Sodium hydride is unsuitable for the production on a large industrial scale since on contact with water highly flammable gases are formed which may spontaneously ignite. Handling of sodium hydride on a large industrial scale requires in particular during feeding into the reaction tank enormous safety precautions and results in high costs and should therefore be avoided if possible. A further disadvantage of this process step is the low yield of 40%.

A disadvantage of the stereoselective hydrogenation to (3R)-4,4,4-trifluoro-3-methylbutanoic acid in process step (X)→(XI) is the expensive catalyst and at the same time poor stereoselectivity requiring subsequent enantiomer enrichment by crystallization as tert-butylammonium salt and resulting in a low total yield.

A further disadvantage of the preparation of the compound of the formula (II) by the process described are the high costs of the ligand required for the palladium-catalyzed arylation reaction (XII)+(XIII)→(XIV).

A further disadvantage is the fact that the compounds (XIV) and (II) prepared by the process described have to be purified by chromatography. These intermediate chromatographic purifications are generally technically highly complex and, owing to the large solvent consumption, cost-intensive and should therefore be avoided, if possible. In addition, there are three solid isolations in process steps (VII)+(IX)→(X) and (X)→(XI) which, performed on an industrial scale, are time-consuming and represent a loss of process efficiency. If possible, these compounds should be employed into the next steps in the form of a solution or an oil.

Ultimately, the preparation of the compound of the formula (II) via the process described is unsuitable owing to the high number of chemical steps, poor selectivity, low total yield (8.7%) and high costs of reagents, catalysts and ligands, in particular for the production on a large industrial scale.

An alternative method for preparing the racemate of the compound of the formula (II) is the method of GB-A 2179941. Scheme 5 illustrates the preparation of the compound of the formula (II) starting with ethyl (4-chlorophenyl)acetate of the formula (XV).

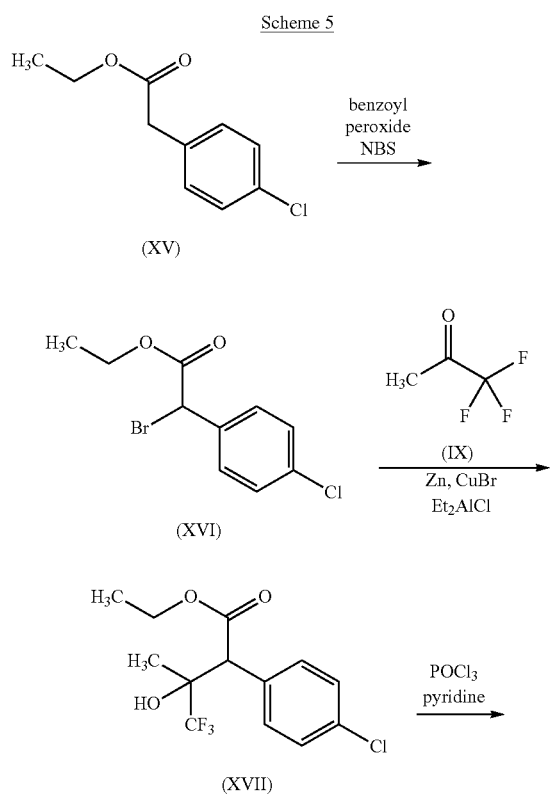

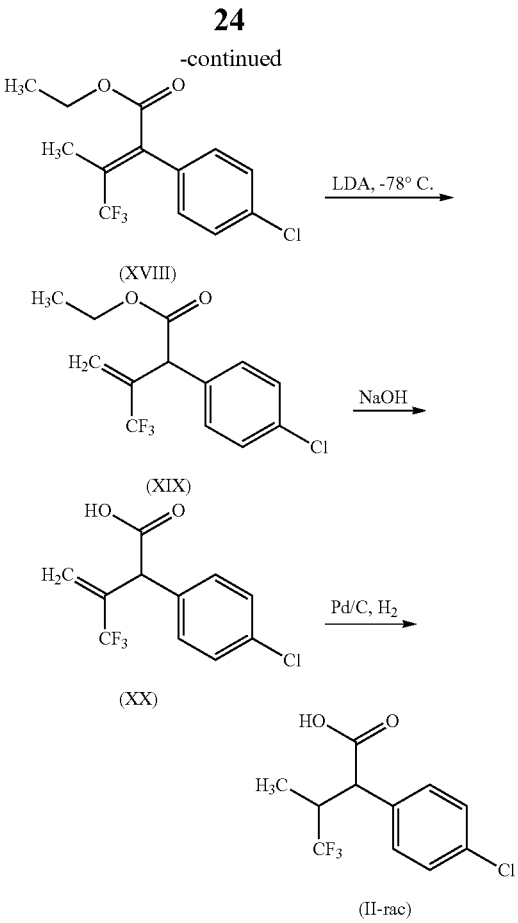

Here, ethyl (4-chlorophenyl)acetate of the formula (XV) is subjected to a free-radical bromination with benzoyl peroxide and N-bromosuccinimide (NBS) in carbon tetrachloride, giving ethyl 2-(4-chlorophenyl)-2-bromoethanoate of the formula (XVI), and the product is, after distillation, obtained in a yield of 76.6%. The bromoester (XVI) is converted in the presence of zinc, copper bromide and diethylaluminium chloride with trifluoroacetone of the formula (XIII) to afford ethyl 2-(4-chlorophenyl)-4,4,4-trifluoro-3-hydroxy-3-methylbutanoate (XVII) which, after chromatography, is obtained in a yield of 81%. (XVII) is then dehydrated with phosphorus oxychloride in pyridine to give ethyl 2-(4-chlorophenyl)-4,4,4-trifluoro-3-methylbut-2-enoate (XVIII) in a yield of 98%. At −78° C., (XVIII) is deprotonated with lithium diisopropylamide (LDA), and methyl 2-(4-chlorophenyl)-4,4,4-trifluoro-3-methylbut-3-enoate (XIX) is obtained after reaction with ammonium chloride and aqueous work-up and chromatographic purification in a yield of 83%. The ester (XIX) is fully hydrolyzed with aqueous sodium hydroxide solution to give the corresponding acid (XX) and catalytically hydrogenated to afford a diastereomer mixture of racemic 4,4,4-trifluoro-3-methylbutanoic acid (II-rac) in quantitative yield. By this process, 4,4,4-trifluoro-3-methylbutanoic acid (II-rac) is obtained as a racemic diastereomer mixture in a total yield of 50%.

A disadvantage of the process of GB-A 2179941 is that reagents such as benzoyl peroxide, N-bromosuccinimide, zinc and also copper salts and alkylaluminium compounds are employed which are either explosive or produce enormous amounts of waste. Thus, benzoyl peroxide undergoes a dangerous decomposition reaction on heating and diethylaluminium chloride is self-igniting on contact with air and forms flammable gases with water. When these reagents are used on an industrial scale, complex and cost-intensive measures for safe handling have to be taken. Zinc is dangerous for the environment and the zinc bromide formed therefrom and also copper bromide are highly toxic to aquatic organisms and may have long-lasting harmful effects in bodies of water. The preparation of 1 kg of the compound of the formula (XVI) requires 1.1 kg of N-bromosuccinimide and the preparation of 1 kg of the compound of the formula (XVII) requires 3.2 kg of 1M diethylaluminium chloride solution and 0.38 kg of zinc. Disposal of these substances requires additional safety precautions and therefore cause high production costs.

A further disadvantage is the fact that, for process step (XV)→(XVI), the toxic and presumably carcinogenic solvent carbon tetrachloride is employed.

A further disadvantage is the fact that the compounds (XVII) and (XIX) prepared by the process described have to be purified by chromatography. These intermediate chromatographic purifications are generally technically highly complex and, owing to the large solvent consumption, cost-intensive and should therefore be avoided, if possible.

A further disadvantage is that the use of palladium results in large-scale dechlorination.

Another disadvantage of this process is that 4,4,4-trifluoro-3-methylbutanoic acid (II-rac) is obtained as a racemic diastereomer mixture and purification of the evaporation residue is not described.

Scheme 6 below illustrates in an exemplary manner the reaction steps of the process according to the invention which yields the compound of the formula (II) in 6 steps without any chromatographic purification of intermediates and end product.

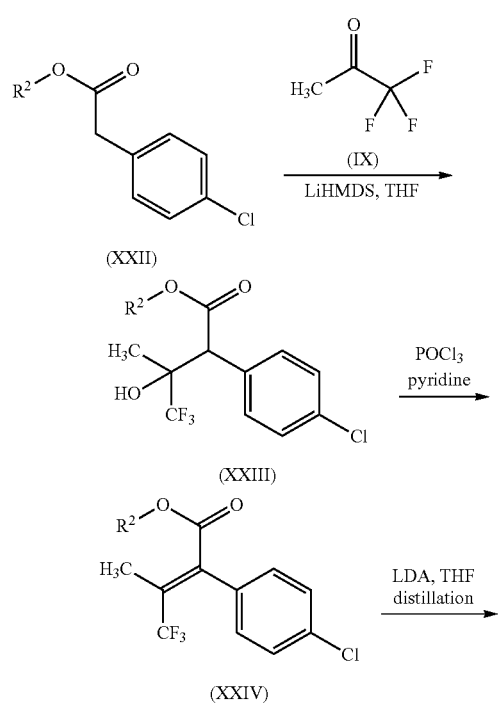

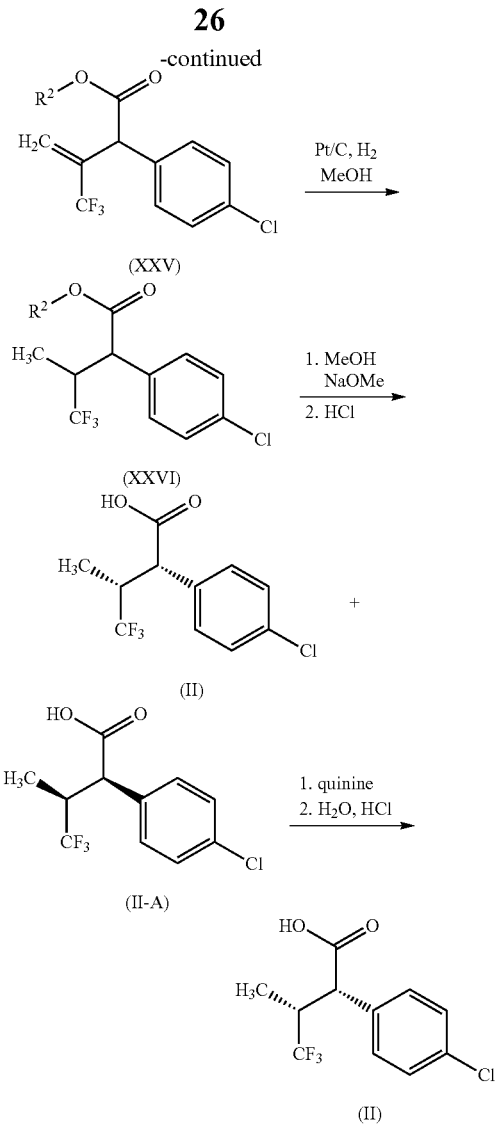

Hereinbelow, the process according to the invention for preparing the compound of the formula (II) is described in detail.

The compound of the formula (XXII) is, at from −30° C. to −78° C., preferably from −65° C. to −78° C., retaliated with a lithium amide base in an inert solvent, and reacted with trifluoroacetone. Suitable lithium amide bases are, for example, lithium hexamethyldisilazide or lithium diisopropylamide (LDA). Surprisingly, it has been found that the reaction with lithium hexamethyldisilazide, compared to LDA, affords a significantly higher yield. Accordingly, the lithium amide base employed is preferably lithium hexamethyldisilazide. Suitable inert solvents are ethers, for example ethylene glycol dimethyl ether (DME), dioxane, tetrahydrofuran (THF), methyltetrahydrofuran or methyl phenyl ether (anisole). Preference is given to using THF. The optimized amounts to be used were determined to be as follows: 1.1 eq of n-BuFi, 1.1 eq of hexamethyldisilazane, 1.5 eq of trifluoroacetone. At most 0° C., the reaction mixture is then hydrolysed with a suitable acid, giving the compound of the formula (XXIII) as an oil. Suitable acids are mineral acids known to the person skilled in the art. Preference is given to using hydrochloric acid, particularly preferably dilute hydrochloric acid (5 N). This gives a diastereomer mixture comprising 0.2% of starting material and 99% of product in a yield of 94%.

The present invention furthermore provides a process for preparing the compound of the formula (XXIII), characterized in that the compound of the formula (XXII)

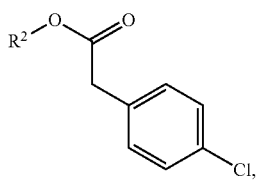
(XXII)

in which $R^2$ represents $(C_1-C_4)$-alkyl, is converted at a temperature of from −30° C. to −78° C., preferably from −65° C. to −78° C., in an inert solvent, preferably tetrahydrofuran, with a lithium amide base, preferably lithium hexamethyldisilazide, and trifluoroacetone into the compound of the formula (XXIII)

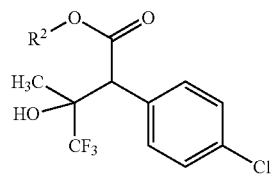
(XXIII)

in which $R^2$ represents $(C_1-C_4)$-alkyl.

For the elimination reaction in process step (XXIII)→(XXIV), use of phosphorus oxychloride in pyridine was surprisingly found to be the system with the best yield. Further experiments with acetyl chloride in triethylamine, acetyl chloride in pyridine, methanesulfonyl chloride in triethylamine, methanesulfonyl chloride in pyridine, sulfuric acid, trifluoromethanesulfonic anhydride, formic acid, T3P (propylphosphoric anhydride) or phosphorus pentoxide gave significantly poorer conversions. The reaction is preferably conducted at reflux temperature. Compared to the prior art in GB-A 2179941, 9 eq or more of pyridine, preferably 9 eq to 15 eq of pyridine, particularly preferably 10 eq to 12 eq of pyridine, very particularly preferably 11 eq of pyridine were employed for the reaction. Surprisingly, this was found to result in enhanced hydrolysability, stirrability and phase separation. These properties are advantageous in particular on an industrial scale for carrying out the reaction in a more efficient manner. In pyridine, the compound of the formula (XXIII) is reacted at reflux with 1 to 3 eq of phosphorus oxychloride, preferably 1.8 eq of phosphorus oxychloride, to yield the compound of the formula (XXIV). For work-up, ethyl acetate is added, the mixture is washed with dilute hydrochloric acid and water, the solution is concentrated and the oil obtained is used for the next step as a solution in THF.

The present invention furthermore provides a process for preparing the compound of the formula (XXIV), characterized in that the compound of the formula (XXIII)

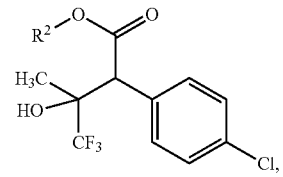
(XXIII)

in which
$R^2$ represents $(C_1-C_4)$-alkyl,
is reacted with phosphorus oxychloride and pyridine, preferably 9 to 15 equivalents of pyridine, particularly preferably 10 to 12 equivalents of pyridine, very particularly preferably 11 equivalents of pyridine, to give the compound of the formula (XXIV)

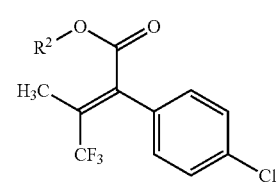
(XXIV)

in which
$R^2$ represents $(C_1-C_4)$-alkyl.

Preferred amounts of phosphorus oxychloride for use in the conversion of the compound of the formula (XXIII) into the compound of the formula (XXIV) are 1 to 5 equivalents.

Particularly preferred amounts of phosphorus oxychloride for use in the conversion of the compound of the formula (XXIII) into the compound of the formula (XXIV) are 1 to 3 equivalents.

Very particularly preferred amounts of phosphorus oxychloride for use in the conversion of the compound of the formula (XXIII) into the compound of the formula (XXIV) are 1.8 equivalents.

The compound of the formula (XXIV) is metallated at from −30° C. to −75° C., preferably from −65 to −75° C., with lithium diisopropylamide (LDA) and protonated with acetic acid in THF. After aqueous work-up, the product is diluted with polyethylene glycol 400 and distilled on a thin film evaporator at a jacket temperature of 145° C. and a pressure of from 1 to 10 mbar.

Optimum isomerization requires 2 eq of LDA. The preparation of LDA from butyllithium and diisopropylamine has been found to be advantageous since, compared to commercial solutions, higher LDA concentrations can be achieved. Experiments with lower amounts used of LDA, lithium chloride/LDA mixtures and lithium bis(trimethylsilyl)amide resulted in lower yields. Work-up of the reaction mixture was found to be particularly critical. Hydrolysis with hydrochloric acid is described in GB 2174491. On an industrial scale, this method leads to a significantly poorer yield than on the laboratory scale. Surprisingly, the yield increases when, initially at from −30° C. to −75° C., preferably from −65 to −75° C., the reaction mixture is acidified with an organic acid in an inert solvent and aqueous work-up is then carried out using a mineral acid at pH 4. Suitable organic acids are organic acids familiar to the person skilled in the art; preference is given to using acetic acid. Suitable inert solvents are, for example, ethylene glycol dimethyl ether (DME), dioxane, tetrahydrofuran (THF), methyltetrahydrofuran or methyl phenyl ether (anisole). Preference is given to using THF. Suitable mineral acids are mineral acids familiar to the person skilled in the art, for example hydrochloric acid or sulfuric acid; preference is given to hydrochloric acid.

The present invention furthermore provides a process for preparing the compound of the formula (XXV), characterized in that the compound of the formula (XXIV)

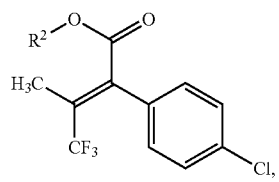
(XXIV)

in which $R^2$ represents $(C_1-C_4)$-alkyl, is reacted with a lithium amide base, preferably lithium diisopropylamide, and the hydrolysis to give the compound of the formula (XXV)

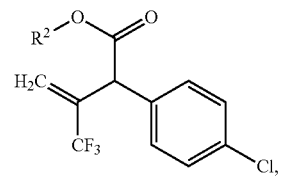
(XXV)

in which $R^2$ represents $(C_1-C_4)$-alkyl, is carried out by adding an organic acid, preferably acetic acid, in an inert solvent, preferably THF, and, in a second step, by adding a mineral acid, preferably hydrochloric acid.

The hydrolysis is preferably carried out at a temperature of from −30° C. to −75° C., preferably from −65° C. to −75° C.

The compound of the formula (XXV) is then hydrogenated in an organic solvent using a platinum catalyst. Suitable organic solvents are alcohols, esters and ethers known as solvents to the person skilled in the art. Preference is given to using methanol. The catalyst used is preferably 5% platinum on carbon, 50% water-wet at from 20° C. to 70° C., preferably 50° C., and at a pressure of from 5 bar to 100 bar, preferably 80 bar. The prior art (GB 2179941) discloses a hydrogenation reaction with palladium. Surprisingly, it was found that the hydrogenation with platinum results in a higher yield since there is less dechlorination of the aromatic system.

The present invention furthermore provides a process for preparing the compound of the formula (II), characterized in that the compound of the formula (XXV)

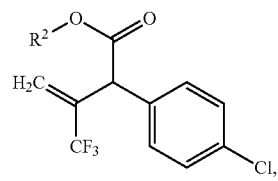
(XXV)

in which $R^2$ represents $(C_1-C_4)$-alkyl, is converted in a hydrogenation reaction into the compound of the formula (XXVI)

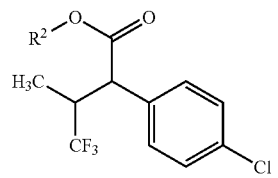
(XXVI)

in which $R^2$ represents $(C_1-C_4)$-alkyl.

The present invention furthermore provides a process for preparing the compound of the formula (XXVI), characterized in that the compound of the formula (XXIV)

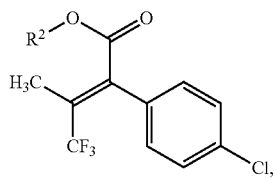
(XXIV)

in which $R^2$ represents $(C_1-C_4)$-alkyl, is reacted with a lithium amide base, preferably lithium diisopropylamide, and the hydrolysis to give the compound of the formula (XXV)

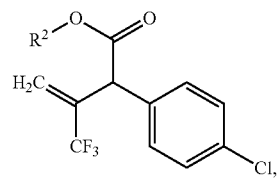
(XXV)

in which $R^2$ represents $(C_1-C_4)$-alkyl, is carried out by addition of an organic acid, preferably acetic acid, in an inert solvent, preferably THF, and in a further step by addition of a mineral acid, and in a further step is converted in a hydrogenation reaction into the compound of the formula (XXVI)

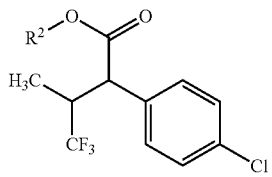

(XXVI)

in which

R² represents (C₁-C₄)-alkyl.

The hydrogenation reaction of the compound of the formula (XXVI) to give the compound of the formula (XXVI) is preferably carried out using platinum catalysis with 5% platinum on carbon.

The hydrogenation reaction of the compound of the formula (XXVI) to give the compound of the formula (XXVI) is particularly preferably carried out using platinum catalysis with 5% platinum on carbon, 50% water-wet at from 20° C. to 70° C. and at a pressure of from 5 bar to 100 bar.

The hydrogenation reaction of the compound of the formula (XXVI) to give the compound of the formula (XXVI) is very particularly preferably carried out using platinum catalysis with 5% platinum on carbon, 50% water-wet at 50° C. and at a pressure of from 5 bar to 100 bar.

The hydrogenation reaction of the compound of the formula (XXVI) to give the compound of the formula (XXVI) is very particularly preferably carried out using platinum catalysis with 5% platinum on carbon, 50% water-wet at 50° C. and at a pressure of 80 bar.

The compound of the formula (XXVI) is isomerized at from 5° C. to 40° C., preferably 20° C., using sodium methoxide, preferably 1.8 eq of sodium methoxide, in methanol, and the ester is hydrolyzed to the sodium salt by addition of water. The sodium salt is isolated by filtration and purified by washing with water. Surprisingly, it has been found that the compound of the formula (XXVI) is isomerized and only the sodium salts of the two compounds (2R,3S)-2-(4-chlorophenyl)-4,4,4-trifluoro-3-methylbutanoic acid of the formula (II-A) and (2S,3R)-2-(4-chlorophenyl)-4,4,4-trifluoro-3-methylbutanoic acid of the formula (II) are poorly soluble in this system. Accordingly, crystallization is suitable for efficient purification. The salts crystallize out with high diastereomer purity, all further impurities such as 4-chlorophenylacetic acid, for example, remain in the mother liquor. For optimization of the isomerization, LDA, Na and K tert-butoxide and the crystallization of the barium salt in various solvents were examined, with little success. The free acid of the compounds of the formulae (II) and (II-A) is obtained by acidification with dilute acids, preferably hydrochloric acid, particularly preferably 20% strength hydrochloric acid. Hereinbelow, a mixture of the two compounds of the formulae (II) and (II-A) is referred to as rel-(2R,3S)-2-(4-chlorophenyl)-4,4,4-trifluoro-3-methylbutanoic acid.

The present invention furthermore provides a process for preparing the compounds of the formulae (II-Na) and (II-A-Na), characterized in that the compound of the formula (XXVI)

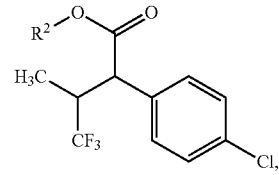

(XXVI)

in which

R² represents (C₁-C₄)-alkyl, is converted with sodium methoxide in methanol and subsequent addition of water into the compounds of the formulae (II-Na) and (II-A-Na)

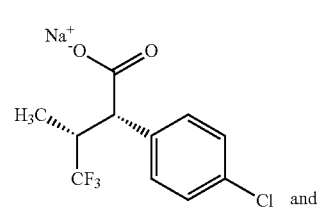

(II-Na)

and

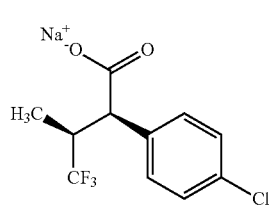

(II-A-Na)

which precipitate as a solid.

The present invention preferably provides a process for preparing the compounds of the formulae (II) and (II-A), characterized in that the compound of the formula (XXVI)

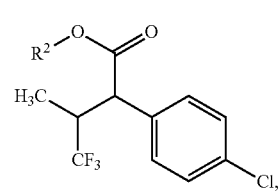

(XXVI)

in which

R² represents (C₁-C₄)-alkyl, is converted with sodium methoxide in methanol and subsequent addition of water into the compounds of the formulae (II-Na) and (II-A-Na)

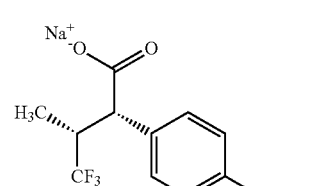

(II-Na)

and

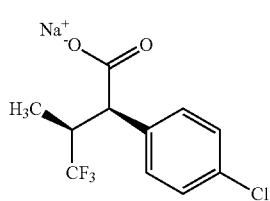

which precipitate as solids and, after isolation, are, by addition of a dilute mineral acid, converted into the compounds of formulae (II) and (II-A)

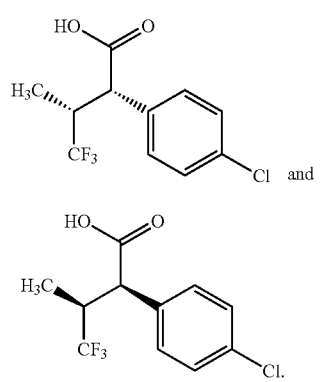

To isolate (2S,3R)-2-(4-chlorophenyl)-4,4,4-trifluoro-3-methylbutanoic acid (II) from the diastereomer mixture obtained above, a solution of rel-(2R,3S)-2-(4-chlorophenyl)-4,4,4-trifluoro-3-methylbutanoic acid in ethanol is metered into a solution of quinine in ethanol at a temperature of from 50° C. to reflux temperature, and the mixture is cooled to from 0° C. to 20° C. In the context of the invention, quinine is the compound of the name (3alpha,4beta,8alpha,9R)-6'-methoxycinchonan-9-ol (CAS number: 130-95-0). Surprisingly, in this system the quinine salt of the compound (2S,3R)-2-(4-chlorophenyl)-4,4,4-trifluoro-3-methylbutanoic acid (II) crystallizes out and the quinine salt of the compound (2R,3S)-2-(4-chlorophenyl)-4,4,4-trifluoro-3-methylbutanoic acid (II-A) remains in solution. Accordingly, this method is suitable for purifying the desired compound of the formula (II). Racemate resolution requires dilutions of from 5 kg to 30 kg of ethanol, preferably 13 kg to 17 kg of ethanol per kilogram of the compound of the formula (II). Preference is given to using 0.3 eq to 1.1 eq of quinine, preferably 0.6 eq to 0.8 eq of quinine, very particularly preferably 0.75 eq of quinine.

The solid is then isolated and washed with ethanol and water. Subsequently, the solid is dissolved in a mixture of water and methanol in a ratio of from 1:1 to 1:5, preferably 1:2 to 1:3, particularly preferably 1:2.7 and cooled. Subsequently, the solid is dissolved in a mixture of water and ethanol in a ratio of from 1:1 to 1:10, preferably 1:4 to 1:5, particularly preferably 1:4.9 and cooled. These steps are preferably carried out at a temperature of from 20° C. to reflux temperature, particularly preferably at a temperature of from 50° C. to reflux temperature.

A dilute mineral acid, preferably hydrochloric acid, particularly preferably 25% strength hydrochloric acid, is added to the suspended quinine salt of the formula (II-Ch), and the solid is isolated, washed with water and dried. Owing to the poor solubility of quinine hydrochloride in water (62.5 g/l of water), the release has to be carried out in appropriate dilution.

The present invention further provides the compound of the formula (II-Ch)

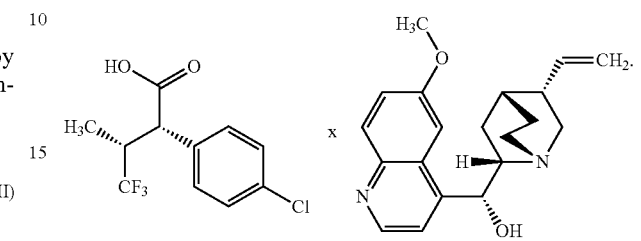

The present invention further provides a substance mixture comprising the compound of the formula (II) and quinine.

The invention further provides a process for purifying the compound of the formula (II), characterized in that the compound of the formula (II), present as quinine salt of the formula (II-Ch), is isolated in an inert solvent.

The present invention furthermore provides a process for preparing the compound of the formula (II-Ch), characterized in that the compound of the formula (II)

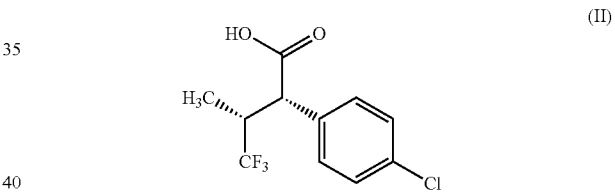

is reacted with a solution of quinine to give the compound of the formula (II-Ch)

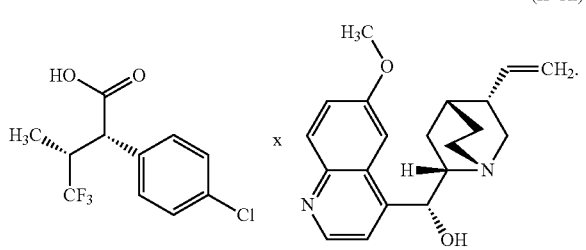

The present invention furthermore provides a process for preparing the compound of the formula (II-Ch) as described above and purification of the compound of the formula (II-Ch) is carried out in a first step by crystallization from a mixture of water and methanol in a ratio of from 1:1 to 1:5, preferably from 1:2 to 1:3, particularly preferably 1:2.7 and in a second step by crystallization from a mixture of water and ethanol in a ratio of from 1:1 to 1:10, preferably from 1:4 to 1:5, particularly preferably 1:4.9.

The present invention furthermore provides a process for preparing the compound of the formula (II), characterized in that
a mixture of the compounds of the formulae (II) and (II-A)

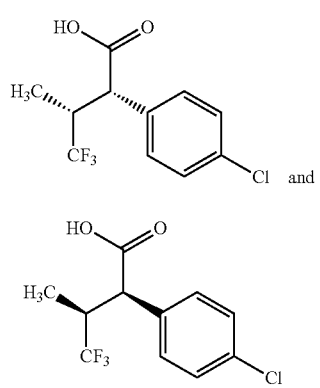

is reacted with a solution of quinine and the isolated compound of the formula (II-Ch)

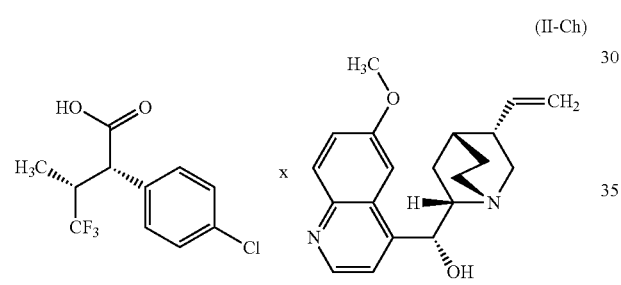

is reacted by addition of dilute mineral acid to the compound of the formula (II)

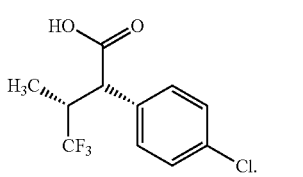

The present invention furthermore provides a process for preparing the compound of the formula (II), characterized in that the compound of the formula (XXVI)

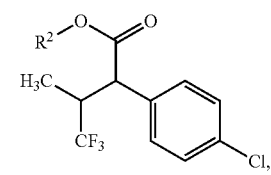

in which
$R^2$ represents $(C_1-C_4)$-alkyl,
is converted with sodium methoxide in methanol and subsequent addition of water into the compounds of the formulae (II-Na) and (II-A-Na)

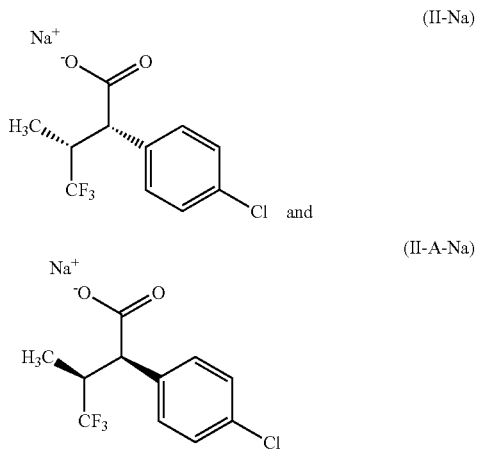

which precipitate as solids and are, by addition of a dilute mineral acid, converted into the compounds of the formulae (II) and (II-A)

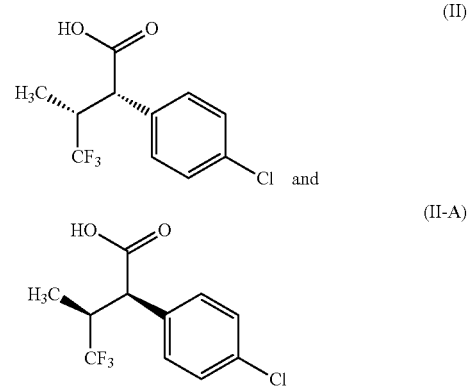

and, in a further step, reacted with a solution of quinine, resulting in the precipitation of the compound of the formula (II-Ch)

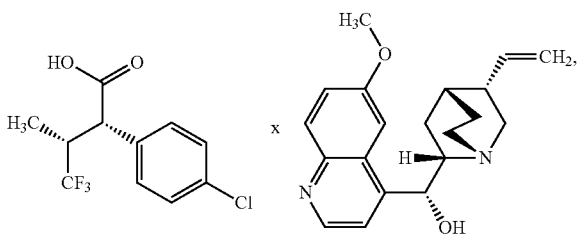

and converted by addition of dilute mineral acid into the compound of the formula (II)

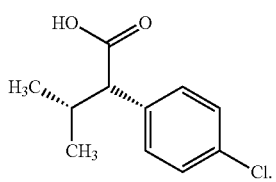
(II)

With regard to the prior art of GB-A 2179941, the process according to the invention for preparing (+)(2S,3R)-2-(4-chlorophenyl)-4,4,4-trifluoro-3-methylbutanoic acid has the following advantages.

The prior art describes the preparation of the compound of the formula (XVII) in a two-step process in a yield of 62%. In the process according to the invention, these two steps can be replaced by an efficient process step (XXII)→(XXIII) using LiHMDS, with a yield of 94%. In addition, the use of benzoyl peroxide, N-bromosuccinimide, benzene, sodium hydride and aluminium alkyl compounds is dispensed with. Diethylaluminium chloride is self-igniting on contact with air and forms flammable gases with water. Also avoided is the use of zinc bromide and copper bromide, both of which are highly toxic to aquatic organisms and may have long-lasting harmful effects in bodies of water. When these reagents are used, special cost-intensive measures for safe handling have to be taken. A further advantage of the use of LiHMDS in process step (XXII)→(XXIII) is that it is no longer necessary to prepare the bromoester of the formula (XVI) by free-radical bromination (XV)→(XVI). This also avoids the high costs associated with the disposal of the reagents and the additional costs for the safety measures required.

Compared to the prior art of GB-A 2179941 and WO 2012/139888, cost- and time-intensive chromatographic purification steps of the intermediates are dispensed with since all intermediates up to the isolation of the racemic acid in process step (XXVI)→(II)+(II-A) are employed for the subsequent step as a solution or a concentrated oil, without further purification.

It is a further advantage that, by using platinum in process step (XV)→(XVI), there is less dechlorination compared to the hydrogenation conditions in GB 2179941.

It is a further advantage that effective purification takes place by crystallization of the compounds (II) and (II-A) as sodium salt. Since up to this reaction step all intermediates are employed for the subsequent step in the form of an oil or a solution, this allows for the removal of all by-products. Chromatographic purification, which is technically highly complex and cost-intensive owing to the high consumption of solvents, can therefore be dispensed with.

Surprisingly, in the crystallization of the compound of the formula (II) as quinine salt, a method has been found by which the compound of the formula (II) can be obtained in high diastereomeric purity and enantiomeric purity so that separation on a chiral column, which is technically highly complex and, owing to the high consumption of solvents, cost-intensive, can be dispensed with.

A further advantage is that, compared to the prior art of [A. Gerlach and U. Schulz, *Speciality Chemicals Magazine* 24 (4), 37-38 (2004); CAS Acc. No. 142:179196] and WO 12/139888, there are no high costs for catalysts and ligands. Compared to the prior art of GB 2179941 and WO 12/139888, isolation and purification operations are dispensed with since the intermediates up to the isolation of the racemic acid are employed for the subsequent step as a solution or a concentrated oil, without further purification.

The term "$C_1$-$C_4$-alkyl" denotes a straight-chain or branched saturated monovalent hydrocarbyl group having 1, 2, 3 or 4 carbon atoms, for example a methyl, ethyl, propyl, isopropyl, butyl, sec-butyl, isobutyl or tert-butyl group.

The present invention furthermore provides for preparing (3S)-3-(3-amino-4-chlorophenyl)-3-cyclopropylpropanoic acid of the formula (VII), which serves as starting material for the preparation of the compound of the formula (I). The compound of the formula (III) represents the corresponding tert-butyl ester of the compound of the formula (VII). The preparation of the compound of the formula (III) is known in principle. WO 2012/139888 describes the preparation of the compound of the formula (III) by the following route (Scheme 7).

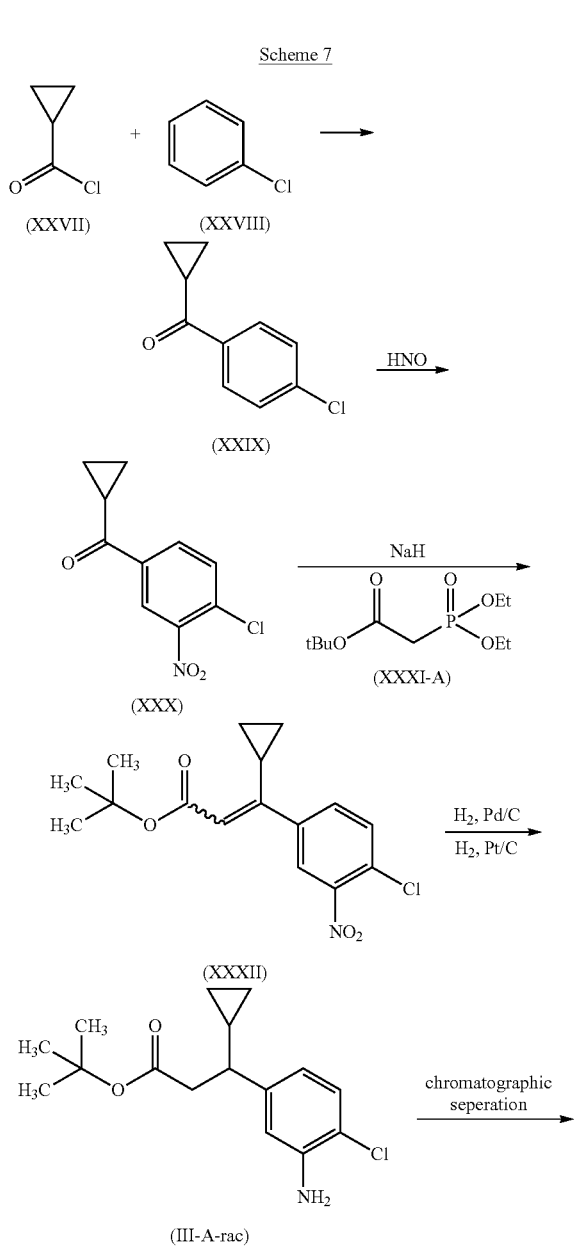

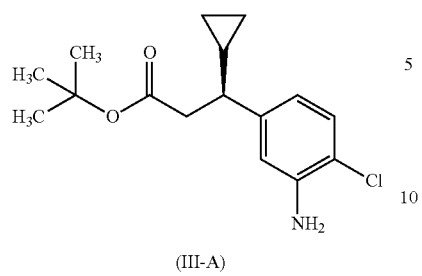

(III-A)

(4-Chlorophenyl)(cyclopropyl)methanone of the formula (XXIX) can be obtained from cyclopropane-carbonyl chloride (XXVII) and chlorobenzene (XXVIII). Nitration of the compound of the formula (XXIX) is carried out under an atmosphere of argon in concentrated nitric acid. The reaction product of the formula (XXX) obtained is isolated and reacted with sodium hydride and tert-butyl (diethoxyphosphoryl)acetate of the formula (XXXI-A) to give tert-butyl (2E/Z)-3-(4-chloro-3-nitrophenyl)-3-cyclopropylacrylate of the formula (XXXII). Catalytic hydrogenation of the isolated and purified reaction product under an atmosphere of hydrogen affords the racemic compound tert-butyl 3-(3-amino-4-chlorophenyl)-3-cyclopropylpropanoate of the formula (III-A-rac). The (S)-enantiomer of the formula (III-A) is obtained by preparative HPLC on a chiral phase.

A disadvantage of the synthesis of the compound of the formula (III-A) is the simultaneous catalytic hydrogenation of the double bond and the nitro group in process step (XXXII)→(III-A-rac) which leads to some unwanted reactions such as opening of the cyclopropane ring or dechlorination of the aromatic.

A considerable disadvantage for a process on an industrial scale is the separation of the enantiomers by preparative HPLC on a chiral phase in process step (III-A-rac)→(III-A). This separation of the enantiomer mixture of the formula (III-rac) by chromatography on a chiral phase was found to be extremely inefficient since repeated chromatography is required for sufficient enantiomeric purity. Owing to the high consumption of solvents and chiral phase, this method is very cost-intensive and furthermore, owing to the additional chromatography cycles in relation to the amount of product, time-consuming, and thus to be judged a low-efficiency process on the industrial scale. Scaling-up of a chromatographic separation of enantiomers to an industrial scale should accordingly be avoided, if possible.

Scheme 8 below illustrates the reaction steps of the process according to the invention in an exemplary manner.

Scheme 8

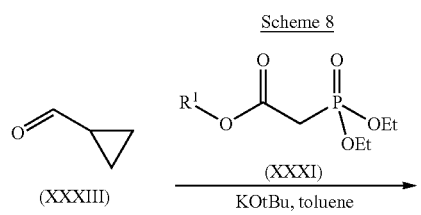

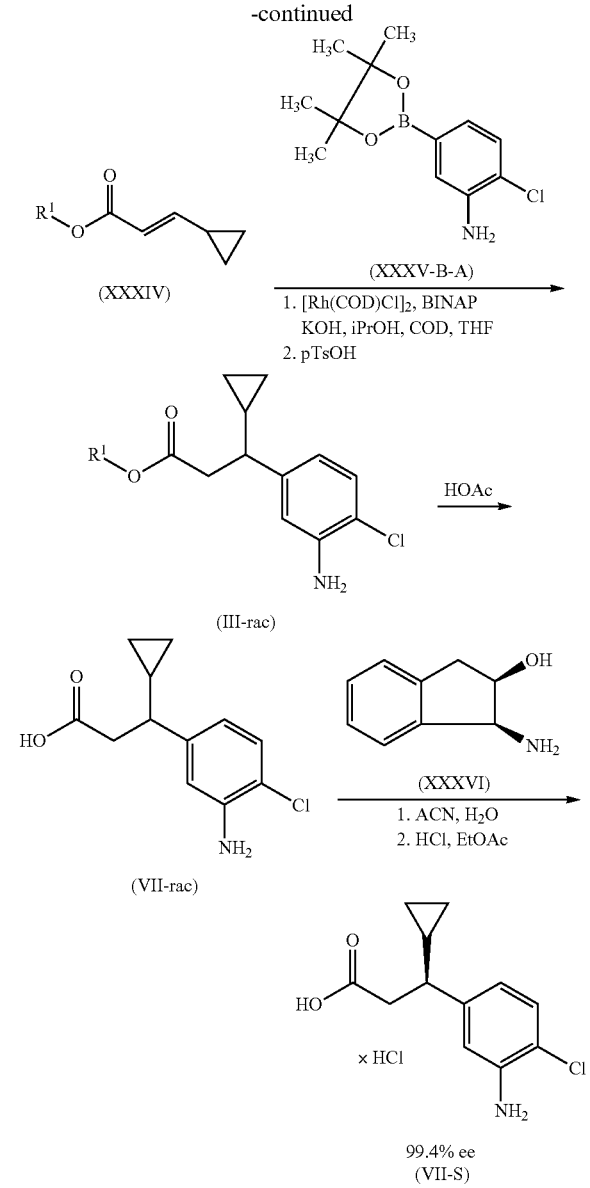

[KOtBu, potassium tert-butoxide: cod, cyclooctadiene; BINAP, (2,2'-bis(diphenylphosphino)-1,1'–binaphthyl); iPrOH, 2-propanol; THF, tetrahydrofuran; pTsOH, p-toluenesulfonic acid; ACN, acetonitrile; EtOAc, ethyl acetate]

Hereinbelow, the process according to the invention for preparing the compound of the formula (VII) is described in detail.

The compound of the formula (XXXIV) is obtained by reacting cyclopropylaldehyde (XXXIII) with tert-butyl diethylphosphonoacetate (XXXI) in toluene with KOtBu at 0° C. to 30° C. After aqueous acidic work-up, the product can be obtained by distillation or crystallization.

The present invention furthermore provides a process for preparing the compound of the formula (XXXIV), characterized in that the compound of the formula (XXXIII)

at from 0 to 30° C. in toluene, potassium tert-butoxide and a compound of the formula (XXXI)

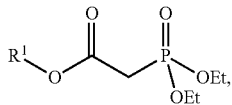
(XXXI)

in which
R¹ represents $(C_1-C_4)$-alkyl,
is converted into the compound of the formula (XXXIV)

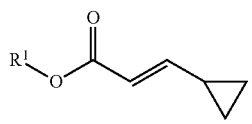
(XXXIV)

in which
R¹ represents $(C_1-C_4)$-alkyl.

The compound of the formula (III-rac) is obtained in a rhodium-catalyzed 1,4-addition of a boronic acid or a boronic ester with the aid of a base, a protic solvent, cyclooctadiene (COD) in THF or toluene, preferably at from 50° C. to 80° C. To this end, the compounds (XXXIV) are initially charged with the boronic ester of the formula (XXXV-B-A) in THF, a protic solvent and a base, under exclusion of air. Instead of the pinacol ester of the formula (XXXV-B-A), it is possible to use other esters of boronic acid known to the person skilled in the art, and also free boronic acid. Protic solvents suitable for these reactions are water or alcohols such as methanol, ethanol, n-propanol, isopropanol, n-butanol or tert-butanol. Preference is given to using isopropanol. Suitable bases are customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to using potassium hydroxide. Preferably at from 50° C. to 80° C., a mixture of (+,−)-BINAP and [Rh(COD)Cl]₂ which has been stirred beforehand for 15 min in the presence of air is added to this suspension. Alternatively, this reaction can also be carried out without (+,−)BINAP. It was found that addition of 1,5-cyclooctadiene permits a lower catalyst loading. After aqueous work-up, the corresponding tosylate salt of the compound of the formula (III-rac) can be precipitated directly. To this end, p-toluenesulfonic acid is added to a solution of the compound of the formula (III-rac) in ethyl acetate (EtOAc), preferably at a temperature of from 15° C. to 20° C. The reaction affords the desired product in very high purity and an excellent yield of 93% of theory.

The present invention furthermore provides a process for preparing the compound of the formula (III-rac), characterized in that the compound of the formula (XXXIV)

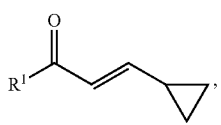
(XXXIV)

in which
R¹ represents $(C_1-C_4)$-alkyl,
is converted with a base, a protic solvent, 1,5-cyclooctadiene, [Rh(COD)Cl]₂ and a compound of the formula (XXXV-A) or (XXXV-B)

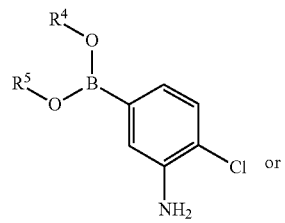
(XXXV-A)

or

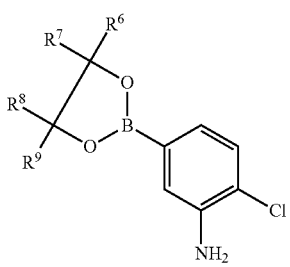
(XXXV-B)

in which
R⁴, R⁵, R⁶, R⁷, R⁸ and R⁹ independently of one another represent hydrogen or $(C_1-C_4)$-alkyl
into the compound of the formula (III-rac)

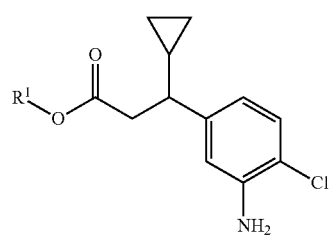
(III-rac)

in which
R¹ represents $(C_1-C_4)$-alkyl.

The present invention furthermore provides a process for preparing the compound of the formula (III-rac), characterized in that the compound of the formula (XXXIV)

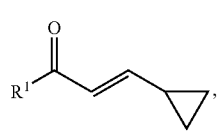
(XXXIV)

in which
R¹ represents $(C_1-C_4)$-alkyl,
with a base, 1,5-cyclooctadiene, (+,−)-BINAP, [Rh(COD)Cl]₂ in the absence of a protective gas with a compound of the formula (XXXV-A) or (XXXV-B)

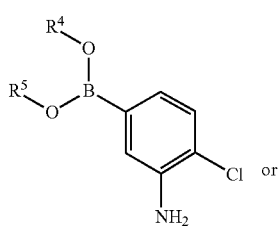
(XXXV-A)

or

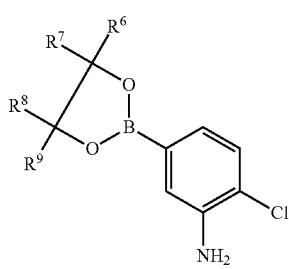
(XXXV-B)

in which

R⁴, R⁵, R⁶, R⁷, R⁸ and R⁹ independently of one another represent hydrogen or $(C_1-C_4)$-alkyl into the compound of the formula (III-rac)

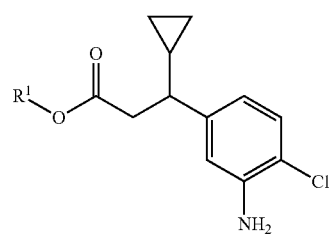
(III-rac)

in which $R^1$ represents $(C_1-C_4)$-alkyl.

The present invention furthermore provides a process for preparing the compound of the formula (VII), characterized in that the compound of the formula (XXXIV)

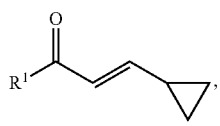
(XXXIV)

in which $R^1$ represents $(C_1-C_4)$-alkyl, is converted with a base, a protic solvent, 1,5-cyclooctadiene, [Rh(COD)Cl]₂ and a compound of the formula (XXXV-A) or (XXXV-B)

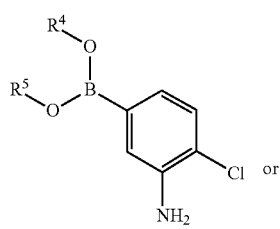
(XXXV-A)

or

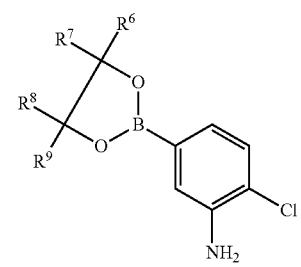
(XXXV-B)

in which

R⁴, R⁵, R⁶, R⁷, R⁸ and R⁹ independently of one another represent hydrogen or $(C_1-C_4)$alkyl into the compound of the formula (III-rac)

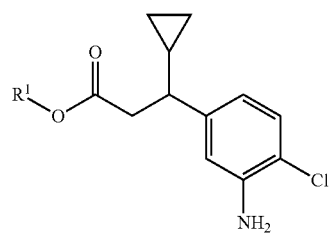
(III-rac)

in which $R^1$ represents $(C_1-C_4)$-alkyl, and, after ester hydrolysis to give the compound of the formula (VII-rac),

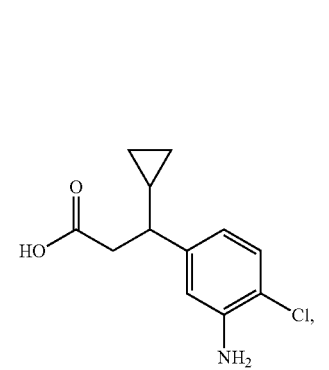
(VII-rac)

reacted with a solution of (1S,2R)-(−)-cis-1-amino-2-indanol to give the compound of the formula (VII-I)

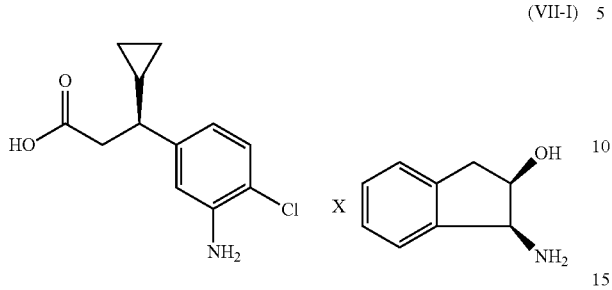
(VII-I)

and in a further step, by addition of dilute mineral acid, the compound of the formula (VII)

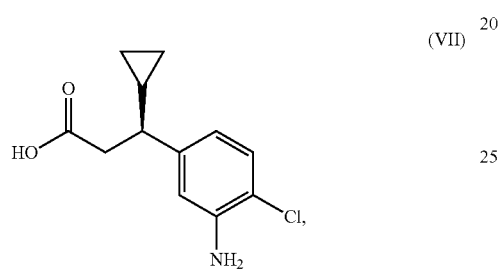
(VII)

or a salt of this compound,
is obtained.

The reaction of the compound of the formula (XXXIV) with a compound of the formula (XXXV-A) or (XXXV-B) preferably takes place in the presence of (+,−)-BINAP and in the absence of a protective gas.

The reaction of the compound of the formula (XXXIV) with a compound of the formula (XXXV-A) or (XXXV-B) preferably takes place at a temperature of from 50° C. to 80° C., particularly preferably at 60° C.

The reaction of the compound of the formula (XXXIV) with a compound of the formula (XXX V-A) or (XXXV-B) preferably takes place with potassium hydroxide as base.

Preferred amounts of 1,5-cyclooctadiene for use in the preparation of the compound (III-rac) are 0.01 eq.

Preferred amounts of (+,−)-BINAP for use in the preparation of the compound (III-rac) are 0.006 eq.

Preferred amounts of [Rh(COD)Cl]$_2$ for use in the preparation of the compound (III-rac) are 0.0025 eq.

The present invention furthermore provides a process for preparing the compound of the formula (III-rac), characterized in that the compound of the formula (XXXIV)

(XXXIV)

in which
R$^1$ represents (C$_1$-C$_4$)-alkyl,
is reacted at 60° C. with potassium hydroxide, isopropanol, catalytic amounts of 1,5-cyclooctadiene, (+,−)-BINAP, 0.0025 eq of [Rh(COD)Cl]$_2$ in the absence of a protective gas with the compound of the formula (XXXV-B-A)

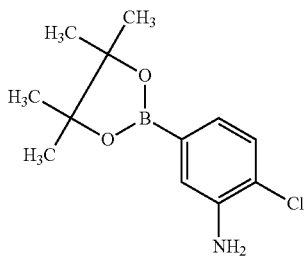
(XXXV-B-A)

to give the compound of the formula (III-rac)

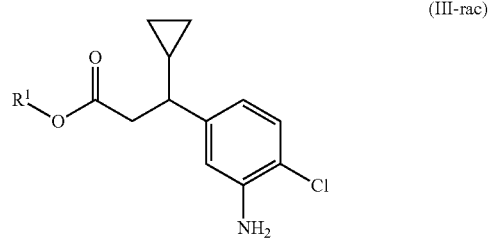
(III-rac)

in which
R$^1$ represents (C$_1$-C$_4$)-alkyl.

Surprisingly, it has been found that the compound of the formula (VH-rac) can be converted by racemate resolution via a corresponding indanol salt of the formula (VII-I) into the enantiomerically pure compound of the formula (VII-C).

To this end, the compound of the formula (VH-rac) is dissolved in acetonitrile and water with heating and (1S, 2R)-(−)-cis-1-amino-2-indanol of the formula (XXXVI) is added. The reaction mixture is seeded and cooled slowly. The product is isolated, resuspended in acetonitrile and water, dissolved with heating and crystallized.

The indanol salt of the formula (VII-I) can be converted into the HCl salt of the formula (VII-S) which corresponds to the compound of the formula (VII) by suspending the indanol salt in EtOAc and water and adding HCl. Following aqueous work-up, the crude solution is concentrated. This crude product is converted in EtOAc with HCl in dioxane into the HCl salt which corresponds to the compound of the formula (VII). The compound of the formula (VII-S) is obtained in an enantiomeric purity of 99.4% in a yield of 37%.

The present invention further provides the compound of the formula (VII-I)

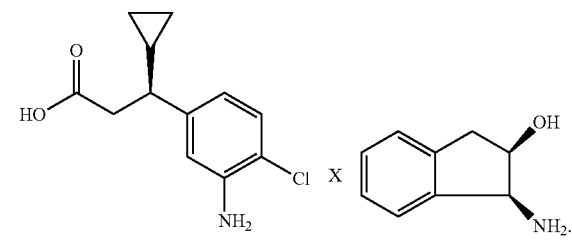
(VII-I)

The present invention further provides a substance mixture comprising the compound of the formula (VII) and (1S,2R)-(−)-cis-1-amino-2-indanol.

The invention further provides a process for purifying the compound of the formula (VII), characterized in that the compound of the formula (VII), present as indanol salt of the formula (VII-I), is isolated in an inert solvent.

The present invention furthermore provides a process for preparing the compound of the formula (VII-I), characterized in that the compound of the formula (VII-rac)

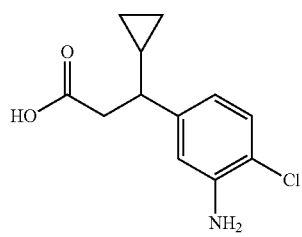

(VII-rac)

is reacted with a solution of (1S,2R)-(−)-cis-1-amino-2-indanol to give the compound of the formula (VII-I)

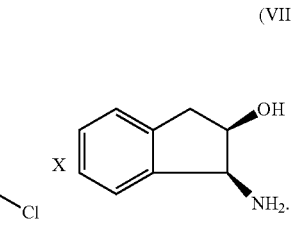

(VII-I)

The present invention furthermore provides a process for preparing the compound of the formula (VII), characterized in that the compound of the formula (VH-rac)

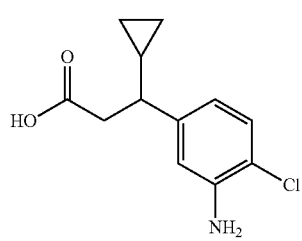

(VII-rac)

is reacted in a mixture of acetonitrile and water in a ratio of from 5:1 to 50:1 with (1S,2R)-(−)-cis-1-amino-2-indanol to give the compound of the formula (VII-I)

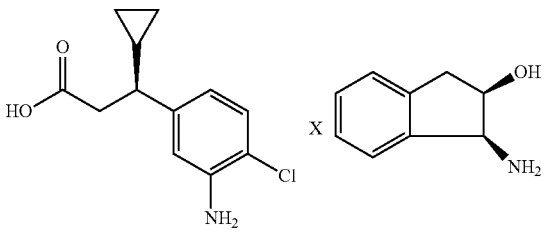

(VII-I)

which, on cooling, precipitates as a solid.

The conversion of the compound of the formula (VH-rac) into the compound of the formula (VII-I) preferably takes place at a temperature of from 30° C. to reflux temperature, particularly preferably at a temperature of from 50° C. to 80° C.

Preferred solvent for the preparation of the compound (VII-I) is a mixture of acetonitrile and water in a ratio of 10:1 to 20:1.

Particularly preferred solvent for the preparation of the compound (VII-I) is a mixture of acetonitrile and water in a ratio of 15:1.

The present invention furthermore provides a process for preparing the compound of the formula (VII), characterized in that the compound of the formula (VII-rac)

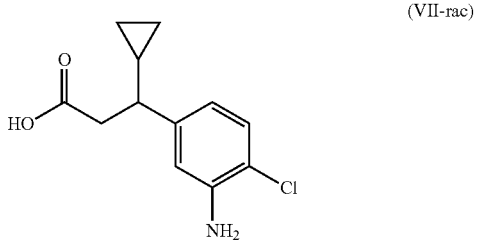 [SMILES: Nc1cc(C(CC(=O)O)C2CC2)ccc1Cl]

(VII-rac)

is reacted with a solution of (1S,2R)-(−)-cis-1-amino-2-indanol to give the compound of the formula (VII-I)

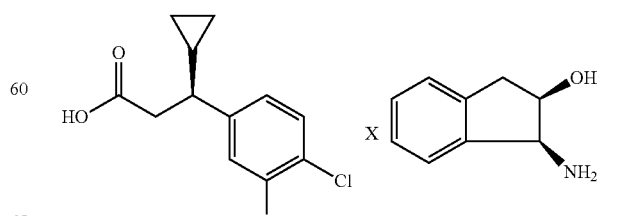

(VII-I)

and converted in a mixture of ethyl acetate and water with hydrochloric acid into the compound of the formula (VII-S)

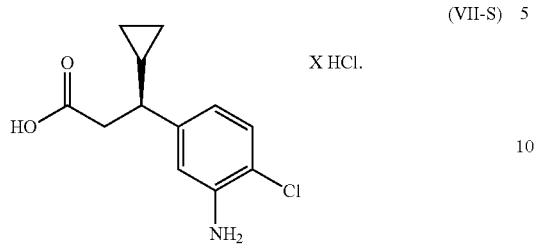

(VII-S)

Compared to the prior art (WO 2012/139888, Example 29A), the cyclopropylpropanoate derivative of the formula (XXXIV) is synthesized by rhodium-catalyzed addition of the boric ester of the formula (XXXV-B-A). The present alternative process has the advantage that, in contrast to the prior art, catalytic hydrogenation ((XXXII)→(III-A-rac)) can be dispensed with. As a result, in total fewer by-products are formed, for example by opening of the cyclopropane ring or by dechlorination of the aromatic, giving higher purity and yield. In addition, for the synthesis of the compound of the formula (III-rac), only one intermediate has to be isolated, which reduces technical expenditure considerably.

The fact that the separation of the enantiomers of the formula (VII-rac) takes place by salt formation with the chiral amine (1S,2R)-(–)-cis-1-amino-2-indanol of the formula (XXXVI) is a further advantage. The prior art (WO 2012/139888, Example 31A) discloses the separation of the enantiomers by preparative HPLC on a chiral column. In the process according to the invention, this technically highly complex and, owing to the high consumption of solvents and chiral phase, cost-intensive method can be dispensed with. Compared to chromatographic separation, scale-up of the crystallization can be carried out in a markedly more efficient manner.

Scheme 9 below illustrates in an exemplary manner the reaction steps of the process according to the invention where the compound of the formula (III) is prepared starting with the compound of the formula (XXXIV) via enantioselective coupling of the boric ester of the formula (XXXV-B-A).

Scheme 9

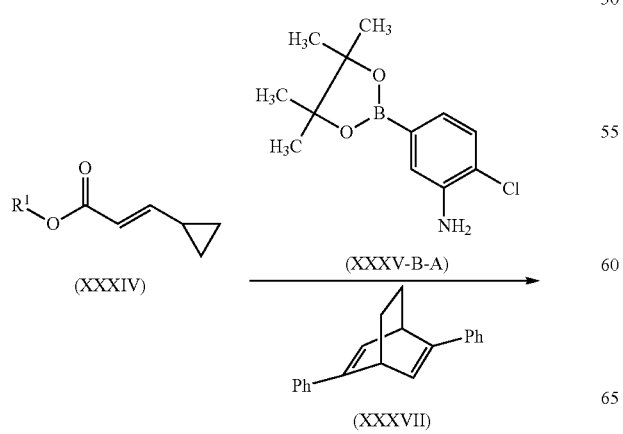

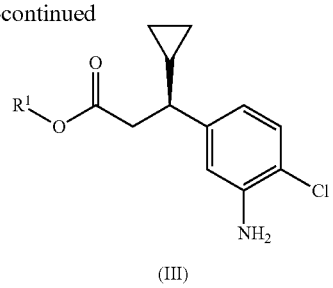

(III)

Hereinbelow, the process according to the invention for preparing the compound of the formula (III) is described in detail.

The catalyst, consisting of a suitable metal precursor and a suitable diene ligand, is stirred in a solvent under exclusion of air. The ratio of metal precursor to diene ligand may be from 1:1 to 1:3; preference is given to using 1:1 or 1:2. Suitable metal precursors are, surprisingly, [Rh(CH$_2$=CH$_2$)$_2$Cl]2, [Rh(coe)$_2$Cl]$_2$ or [Rh(acac)(CH$_2$=CH$_2$)$_2$], where coe means cyclooctene and acac means acetylacetonato. Preference is given to using [Rh(CH$_2$=CH$_2$)$_2$Cl]$_2$. Suitable diene ligands are (1S,4S)-2,5-diphenylbicyclo[2.2.2]octa-2,5-diene (XXXVII); ((3aR,6aR)-3,6-diphenyl-1,3a,4,6a-tetrahydropentalene (XXXVIII); (1S,4S,7S)-α,α,5-trimethyl-7-(1-methylethyl)bicyclo[2.2.2]octa-2,5-diene-2-methanol (XXXIX); 2-naphthyl (1S,4S,7S)-7-isopropyl-5-methylbicyclo[2.2.2]octa-2,5-diene-2-carboxylate (XXXXI) or (1S,4S,8S)-5-benzyl-2-isobutyl-8-methoxy-1,8-dimethylbicyclo[2.2.2]octa-2,5-diene (XXXX). Preference is given to using (1S,4S)-2,5-diphenylbicyclo[2.2.2]octa-2,5-diene of the formula (XXXVII).

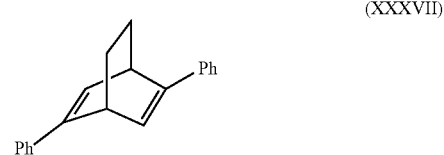

(XXXVII)

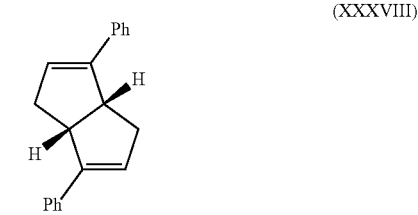

(XXXVIII)

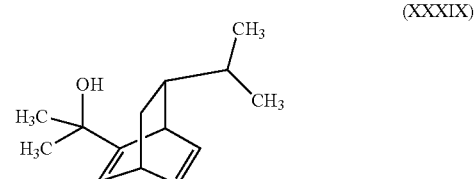

(XXXIX)

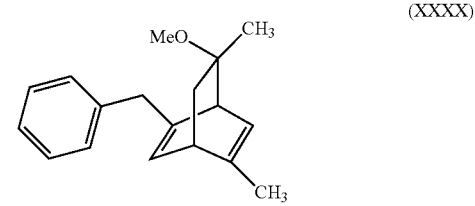

(XXXX)

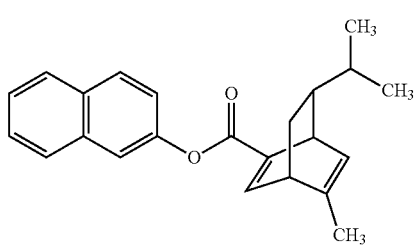

(XXXXI)

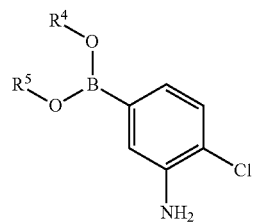

(XXXV-A)

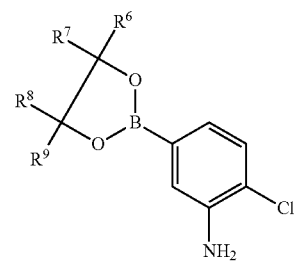

(XXXV-B)

Suitable solvents are methanol, dioxane, isopropanol, THF, water or mixtures thereof. Preference is given to using methanol. In a separate reaction, a suspension of the compounds of the formula (XXXIV) and a boronic ester of the formula (XXXV-B-A) is heated in a solvent and a suitable base to from 40° C. to 110° C., preferably 50° C. Instead of the pinacol ester of the formula (XXXV-B-A), it is possible to use other esters of boronic acid known to the person skilled in the art, and also free boronic acid. Suitable solvents are methanol, dioxane, isopropanol, THF, water or mixtures thereof. Preference is given to using a mixture of methanol and water, particularly preferably a mixture of methanol and water in a ratio of 10:1. Suitable bases are KOH, $K_2CO_3$, $NaHCO_3$ or triethylamine; preference is given to using KOH. After aqueous work-up, the corresponding tosylate can be isolated in good yield and high enantiomeric purity.

WO 2007/057643 illustrates the reaction of fluorinated phenylboronic acids or their esters with α,β-unsaturated propenoic ester derivatives in the presence of chiral rhodium (I) catalyst complexes and a base. In the prior art, the selection of the desired enantiomer takes place by racemate resolution, so that on separation of the enantiomers more than half of the product has to be discarded. Accordingly, the maximum yield in this step is 50%. In the present process according to the invention, the desired enantiomer is formed directly in an enantioselective reaction step in a yield of 77% and an enantiomeric purity of 97.1%.

In the process according to the invention, the separation of the enantiomers by preparative HPLC on a chiral phase, which is technically highly complex and, owing to the high consumption of solvents and chiral phase, cost-intensive, can be dispensed with. Compared to chromatographic separation, scale-up of the enantioselective reaction can be carried out in a markedly more efficient manner.

The present invention furthermore provides a process for preparing the compound of the formula (III), characterized in that the compound of the formula (XXXIV)

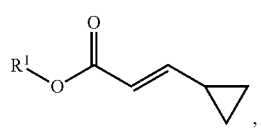

(XXXIV)

in which
$R^1$ represents $(C_1-C_4)$-alkyl,
is converted, with exclusion of oxygen, preferably at a temperature of from 40° C. to 110° C., with a suitable metal precursor, a suitable diene ligand, a suitable base and a compound of the formula (XXXV-A) or (XXXV-B)

in which
$R^4$, $R^5$, $R^6$, $R^7$, $R^8$ and $R^9$ independently of one another represent hydrogen or $(C_1-C_4)$-alkyl
into the compound of the formula (III)

(III)

in which
$R^1$ represents $(C_1-C_4)$-alkyl.

The metal precursor for preparing the compound of the formula (III) is preferably $[Rh(CH_2{=}CH_2)_2Cl]2$, $[Rh(coe)_2Cl]_2$ or $[Rh(acac)(CH_2{=}CH_2)_2]$, the diene ligands are preferably the compounds of the formula (XXXVII), (XXXVIII), (XXXIX), (XXXX) and (XXXXI) and the base is preferably KOH, $K_2CO_3$, $NaHCO_3$, $NaHCO_3$ or triethylamine.

Particularly preferably, the metal precursor for preparing the compound of the formula (III) is $[Rh(CH_2{=}CH_2)_2Cl]_2$, the diene ligand is (1S,4S)-2,5-diphenylbicyclo[2.2.2]octa-2,5-diene (XXXVII) and the base is KOH.

The disclosure also provides all combinations of the metal precursors and diene ligands mentioned for the preparation of the compound of the formula (III).

The present invention furthermore provides a process for preparing the compound of the formula (III), characterized in that the compound of the formula (XXXIV)

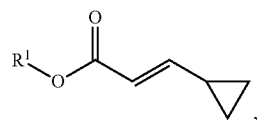

(XXXIV)

in which

R¹ represents $(C_1-C_4)$-alkyl, is converted at a temperature of from 40° C. to 110° C., preferably at a temperature of 50° C., with [Rh(CH₂=CH₂)₂Cl]₂, (1S,4S)-2,5-diphenylbicyclo[2.2.2]octa-2,5-diene of the formula (XXXVII), KOH and a compound of the formula (XXXV-A) or (XXXV-B)

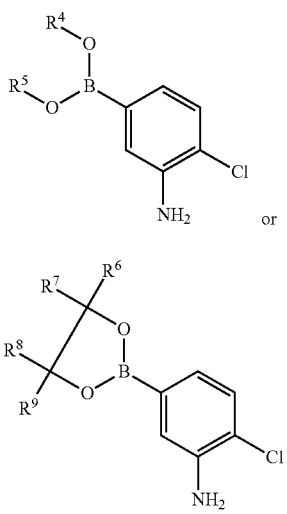

(XXXV-A)

or (XXXV-B)

in which

R⁴, R⁵, R⁶, R⁷, R⁸ and R⁹ independently of one another represent hydrogen or $(C_1-C_4)$-alkyl into the compound of the formula (III)

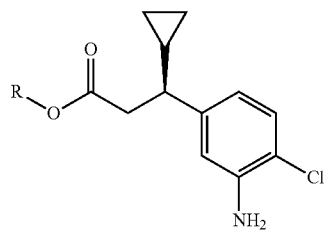

(III)

in which

R¹ represents $(C_1-C_4)$-alkyl.

The conversion of the compound of the formula (XXXIV) into the compound of the formula (III) is preferably carried out using a compound of the formula (XXXV-B-A).

The stated equivalents (eq) for the reactants refer to the molar ratio of this substance based on the starting material to be reacted.

The present invention also provides combinations of the partial reactions introduced above for preparing the compound of the formula (I) in crystalline modification 1 (I-1).

WO 2012/139888 discloses the compound of the formula (I) as an amorphous solid. FIG. 1 shows an X-ray diffractogram of the compound of the formula (I) prepared according to the synthesis described in WO 2012/139888. For the development of a medicinal form comprising the compound of the formula (I) in solid form, there is a high demand for the reproducible isolation of the compound of the formula (I) in a defined crystalline form. Using the process described above, it was possible to isolate the compound of the formula (I) in crystalline form of modification 1 (I-1). Surprisingly, the crystalline form of modification 1 (I-1) shows reproducible bioavailability, better properties for the formulation of medicinal forms and higher thermodynamic stability.

The compound (I) in crystalline modification 1 (I-1) is notable for higher stability and more particularly for the fact that it is stable in the micronization process and hence no conversion and recrystallization takes place.

Figure 2:
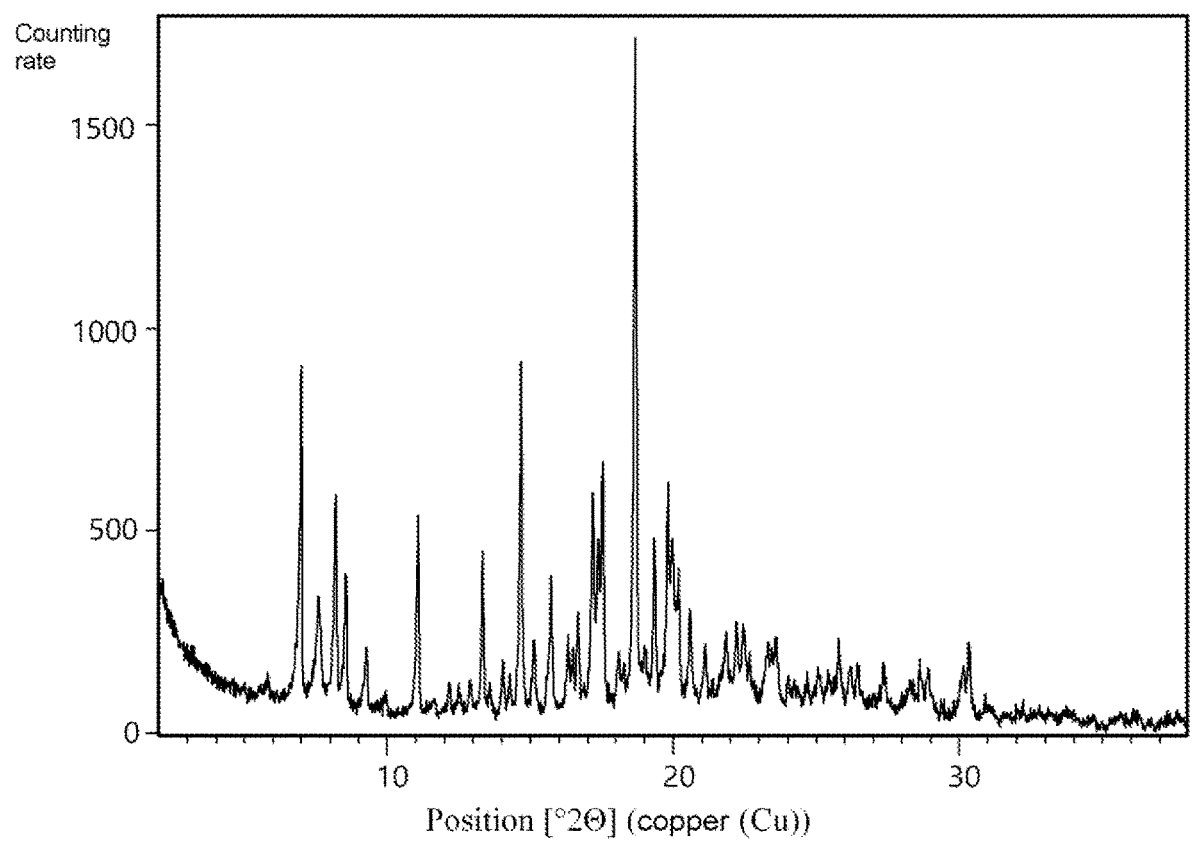

The compound of the formula (I) can be prepared by processes described above. Modification 1 (I-1) has a characteristic x-ray diffractogram characterized by the reflections (2 theta) 7.0; 8.2; 11.1; 14.7; 17.2; 17.5; 18.7 and 19.8 and a characteristic IR spectrum characterized by the band maxima (in cm⁻¹) 1709, 1660, 1534, 1491, 1263, 1167, 1131, 1093 and 1016 (Tables 1 and 2, FIGS. 1 and 2).

Measuring Parameters of the x-Ray Diffractometry for the Analysis of the Compound of the Formula (I) in Amorphous Form and Crystalline Form of Modification 1 (I-1):

| Anode material | Cu |
|---|---|
| K-alpha1 [Å] | 1.54060 |
| Generator setting | 40 mA, 40 kV |

Primary Beam Monochromator Focusing X-Ray Mirror

| Sample rotation | yes |
|---|---|
| Scan axes | Gonio |
| Start position [°2 Th.] | 2.0066 |
| End position [°2 Th.] | 37.9906 |

TABLE 1

X-ray diffractogram of the compound of the formula (I) in modification 1 (I-1)
Reflections
Modification 1

| |
|---|
| 5.7 |
| 7.0 |
| 7.6 |
| 8.2 |
| 8.6 |
| 9.3 |
| 9.9 |
| 11.1 |
| 11.6 |
| 12.2 |
| 12.5 |
| 12.9 |
| 13.3 |
| 13.6 |
| 14.0 |
| 14.3 |
| 14.7 |
| 15.1 |
| 15.7 |
| 16.3 |
| 16.5 |
| 16.6 |
| 17.2 |
| 17.4 |
| 17.5 |
| 18.1 |
| 18.7 |
| 19.0 |
| 19.3 |
| 19.8 |
| 20.0 |
| 20.2 |
| 20.6 |

TABLE 1-continued

X-ray diffractogram of the compound of the
formula (I) in modification 1 (I-1)
Reflections
Modification 1

| |
|---|
| 21.1 |
| 21.8 |
| 22.2 |
| 22.5 |
| 22.7 |
| 23.3 |
| 23.6 |
| 24.0 |
| 24.1 |
| 24.7 |
| 25.0 |
| 25.4 |
| 25.8 |
| 26.2 |
| 26.5 |
| 27.3 |
| 28.3 |
| 28.6 |
| 28.9 |
| 29.4 |
| 30.1 |
| 30.3 |
| 30.9 |
| 31.6 |
| 33.8 |
| 34.6 |
| 35.5 |
| 36.3 |

Measuring Conditions for the IR Spectroscopy for the Measurement of the Compound of the Formula (I) in Crystalline Form of Modification 1 (I-1):

IR:

| | |
|---|---|
| Instrument | Bruker Tensor 37 |
| Number of scans | 64 |
| Resolution | 2 cm$^{-1}$ |
| Aperture | 4 mm |
| Technique | Diamond ATR unit |

TABLE 2

IR spectra of the compound of the
formula (I) in modification 1 (I-1)
Band maximum [cm$^{-1}$]
Modification 1

| |
|---|
| 3234 |
| 3191 |
| 3036 |
| 3004 |
| 2948 |
| 2911 |
| 1709 |
| 1660 |
| 1598 |
| 1534 |
| 1491 |
| 1463 |
| 1415 |
| 1385 |
| 1349 |
| 1323 |
| 1294 |
| 1263 |
| 1245 |
| 1213 |
| 1167 |
| 1131 |
| 1093 |
| 1082 |
| 1054 |
| 1016 |
| 987 |
| 938 |
| 917 |
| 891 |
| 854 |
| 843 |
| 823 |
| 794 |
| 776 |
| 752 |
| 736 |
| 715 |
| 684 |
| 667 |
| 624 |
| 594 |
| 567 |

FIG. 1: X-ray diffractogram of the compound of the formula (I) in amorphous form FIG. 2: X-ray diffractogram of the compound of the formula (I) in modification 1 (I-1)

Figure 3:
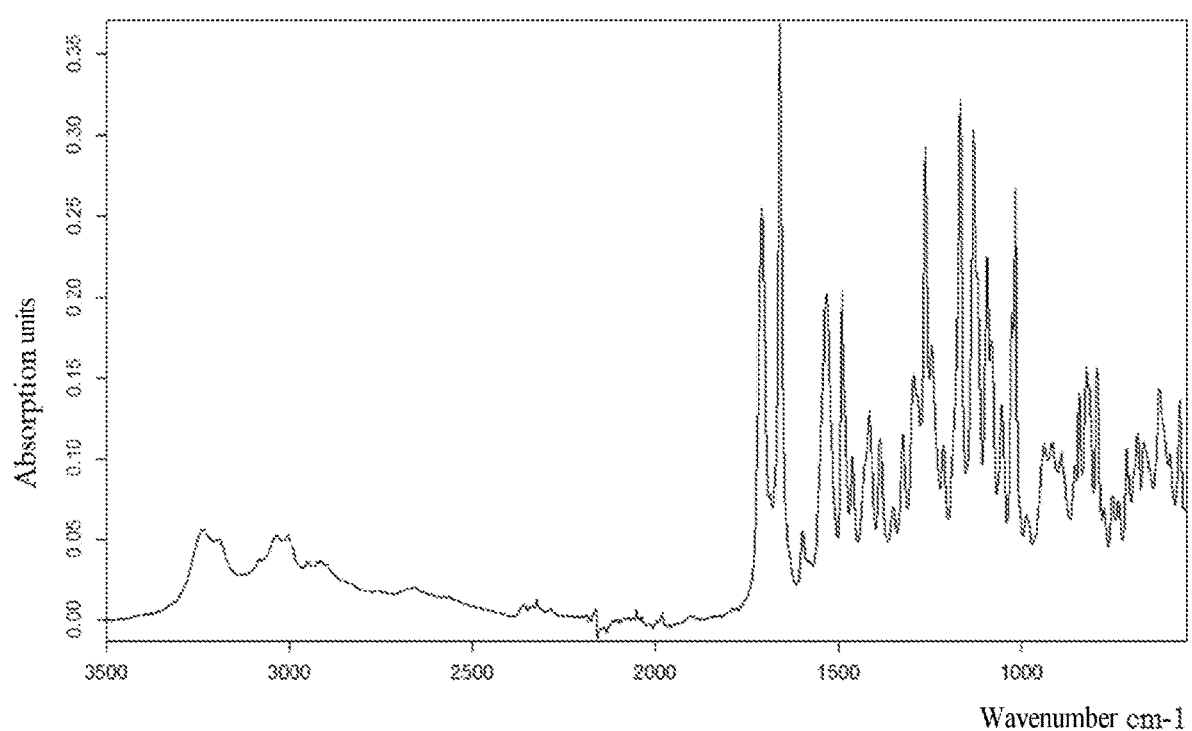

FIG. 3: IR spectrum of the compound of the formula (I) in modification 1 (I-1)

The compounds according to the invention, the compound of the formula (I) and its compound of the formula (I) in crystalline form of modification 1 (I-1) act as activator of soluble guanylate cyclase and exhibit an unforeseeable, useful spectrum of pharmacological activity. They are therefore suitable for use as medicaments for treatment and/or prophylaxis of diseases in humans and animals.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The compounds according to the invention are potent activators of soluble guanylate cyclase. They lead to vascular relaxation, inhibition of platelet aggregation and lowering of blood pressure, and they also increase coronary blood flow and microcirculation. These effects are mediated by a direct, haem-independent activation of soluble guanylate cyclase and an intracellular rise in cGMP.

The compounds according to the invention are especially suitable for treatment and/or prevention of cardiovascular, cardiopulmonary, cardiorenal, thromboembolic, fibrotic and pulmonary disorders.

Accordingly, the compounds of the invention can be used for treatment and/or prevention of cardiovascular and cardiopulmonary disorders, for example high blood pressure (hypertension), heart failure, coronary heart disorders and unstable angina pectoris, pulmonary arterial hypertension (PAH) and secondary forms of pulmonary hypertension (PH), renal hypertension, peripheral and cardiovascular disorders, arrhythmias, rhythm disorders of the atria and ventricles, and conduction disorders, for example atrioventricular blocks of degrees I-III, supraventricular tachycardia, atrial fibrillation, atrial flutter, ventricular fibrillation, ventricular flutter, ventricular tachycardia, Torsade de pointes tachycardia, atrial and ventricular extrasystoles, AV-junctional extrasystoles, sick sinus syndrome, syncopes, AV nodal reentrant tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, and also for treatment and/or prevention of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

Owing to their activity profile, the compounds of the invention are also suitable for the prophylaxis and/or treatment of various disorders and disease-related states, in particular for the treatment and/or prophylaxis of primary and secondary forms of pulmonary hypertension, of acute pulmonary hypertension, in particular acute respiratory distress syndrome (ARDS), acute lung injury (ALI) and infant respiratory distress syndrome (IRDS), heart failure, angina pectoris, hypertension, thromboembolic disorders, ischaemias, vascular disorders, microcirculation impairments, renal insufficiency, fibrotic disorders and arteriosclerosis.

In the context of the present invention, the term "pulmonary hypertension" includes both primary and secondary sub-forms thereof as defined according to the Dana Point classification in accordance with their respective etiology (D. Montana and G. Simonneau et al.: A. J. Peacock et al. (Eds.), *Pulmonary Circulation. Diseases and their treatment*, $3^{rd}$ edition, Hodder Arnold Publ. 2011, pp. 197-206; Hoeper M. M. et al. 2009). These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (IFD), pulmonary fibrosis (IPF), and/or hypoxaemia (e.g. sleep apnoea syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumour disorders, parasites, foreign bodies). Fess common forms of pulmonary hypertension, such as in patients suffering from sarcoidosis, histiocytosis X or lymphangiomatosis, are summarized in group 5.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure, heart failure with reduced ejection fraction (HFrEF), heart failure with preserved ejection fraction (HFpEF).

In addition, the compounds according to the invention can also be used for treatment and/or prevention of arteriosclerosis, impaired lipid metabolism, hypolipoproteinaemias, dyslipidaemias, hypertriglyceridaemias, hyperlipidaemias, combined hyperlipidaemias, hypercholesterolaemias, abetalipoproteinaemia, sitosterolaemia, xanthomatosis, Tangier disease, adiposity, obesity and metabolic syndrome.

The compounds according to the invention can additionally be used for treatment and/or prevention of primary and secondary Raynaud's phenomenon, microcirculation impairments, claudication, hearing disorders, tinnitus, peripheral and autonomic neuropathies, diabetic microangiopathies, diabetic neuropathies, diabetic retinopathy, diabetic ulcers on the extremities, diabetic foot syndrome, gangrene, CREST syndrome, erythematosis, onychomycosis and rheumatic disorders.

In addition, the compounds according to the invention can be employed for the prevention of ischaemia- and/or reperfusion-related damage to organs or tissues and as additives for perfusion and preservation solutions for organs, organ parts, tissues or tissue parts of human or animal origin, in particular for surgical interventions or in the field of transplantation medicine.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof (chronic kidney disease; CKD) and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, diabetic kidney disease (DKD), proteinuric renal disorders, chronic renal insufficiency induced by acute renal failure, pyelonephritis, renal cysts, nephrosclerosis, focal segmental glomerulosclerosis (FSGS), hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the compounds of the invention for treatment and/or prevention of sequelae of renal insufficiency, for example hypertension, pulmonary oedema, heart failure, uraemia, anaemia, electrolyte disturbances (for example hyperkalaemia, hyponatraemia) and disturbances in carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention are also suitable for treatment and/or prevention of asthmatic disorders, chronic obstructive pulmonary disorders (COPD), acute respiratory syndrome (ARDS) and acute lung damage (ALI), alpha-1-antitrypsin deficiency (AATD), pulmonary fibrosis, idiopathic pulmonary fibrosis (IPF), pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. In particular, they are suitable for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), posttraumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prevention of central nervous system disorders such as states of anxiety, tension and depression, CNS-related sexual dysfunctions and sleep disturbances, and for controlling pathological disturbances of the intake of food, stimulants and addictive substances.

In addition, the compounds of the invention are also suitable for controlling cerebral blood flow and are thus effective agents for controlling migraine. They are also suitable for the prophylaxis and control of sequelae of cerebral infarct (Apoplexia cerebri) such as stroke, cerebral ischaemias and craniocerebral trauma. The compounds of the invention can likewise be employed for controlling states of pain.

In addition, the compounds of the invention have anti-inflammatory action and can therefore be used as anti-inflammatory agents for treatment and/or prevention of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

The compounds of the invention are also suitable for treatment and/or prevention of fibrotic disorders of the internal organs, for example the lung, the heart, the kidneys, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, systemic sclerosis, morphea, keloids, hypertrophic scarring, naevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for ageing and keratinized skin.

Furthermore, the compounds of the invention are suitable for treatment and/or prevention of ophthalmological disorders which, for the purposes of the invention, should be understood to mean, for example, the following disorders: age-related macular degeneration (AMD) including dry (non-exudative) and wet (exudative, neovascular) AMD, choroidal neovascularization (CNV), choroidal neovascular membranes (CNVM), cystoid macular oedema (CME), epiretinal membranes (ERM) and macular perforations, myopia-associated choroidal neovascularization, angioid and vascular streaks, retinal detachment, diabetic retinopathy, diabetic macular oedema (DME), atrophic and hypertrophic lesions in the retinal pigment epithelium, retinal vein occlusion, choroidal retinal vein occlusion, macular oedema, macular oedema associated with retinal vein occlusion, Retinitis pigmentosa, Stargardt disease, retinopathy of prematurity, glaucoma, inflammation disorders of the eye, for example uveitis, scleritis or endocarditis, cataract, refraction anomalies, for example myopia, hyperopia, astigmatism or keratoconus, corneal angiogenesis resulting, for example, from keratitis, corneal transplant or keratoplasty, corneal angiogenesis resulting from hypoxia (for example through extensive wearing of contact lenses), conjunctival pterygium, subcorneal oedema and intracorneal oedema.

By virtue of their activity profile, the compounds of the invention are suitable in particular for the treatment and/or prevention of cardiovascular and cardiopulmonary disorders such as primary and secondary forms of pulmonary hypertension, heart failure, angina pectoris and hypertension and also of thromboembolic disorders, ischaemias, vascular disorders, impaired microcirculation, renal insufficiency, fibrotic disorders and arteriosclerosis.

The present invention further provides for the use of the compounds according to the invention for the treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds of the invention.

The present invention further provides a process for treatment and/or prevention of sickle cell anaemia, where traumatized patients receive a synthetic blood substitute, and for preservation of blood substitutes.

The present invention further provides for the use of the compounds according to the invention for treatment and/or prevention of disorders, especially of the aforementioned disorders, where a liquid aerosol is produced using an aerosol generator.

The present invention further provides for the use of the compounds according to the invention for treatment and/or prevention of disorders, especially of the aforementioned disorders, where the addition of β-cyclodextrin, selected from a list comprising unsubstituted β-cyclodextrin, methyl-β-cyclodextrin and (2-hydroxypropyl)-β-cyclodextrin, to the pharmaceutical formulation does not change systemic blood pressure.

The present invention further provides for the use of the compounds according to the invention for treatment and/or prevention of disorders, especially of the aforementioned disorders, where the addition of β-cyclodextrin, selected from a list comprising unsubstituted β-cyclodextrin, methyl-β-cyclodextrin and (2-hydroxypropyl)-β-cyclodextrin, to the pharmaceutical formulation does not change the pharmacokinetic profile of the compound of the formula (I).

The compounds according to the invention can be used alone or, if required, in combination with other active compounds. The present invention further provides medicaments comprising at least one of the compounds of the invention and one or more further active compounds, especially for the treatment and/or prophylaxis of the aforementioned disorders. Preferred examples of active compounds suitable for combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 4 inhibitors such as roflumilast or revamilast and PDE 5 inhibitors such as sildenafil, vardenafil, tadalafil, udenafil, dasantafil, avanafil, mirodenafil or lodenafil;

NO-independent but haem-dependent stimulators of guanylate cyclase, especially riociguat, nelociguat, vericiguat and those in WO 00/06568, WO 00/06569, WO 02/42301, WO 03/095451, WO 2011/147809, WO 2012/004258, WO 2012/028647 and WO 2012/059549;

prostacyclin analogues and IP receptor agonists, by way of example and with preference iloprost, beraprost, treprostinil, epoprostenol, NS-304, selexipag or ralinepag;

endothelin receptor antagonists, by way of example and with preference bosentan, darusentan, ambrisentan, macicentan or sitaxsentan;

inhibitors of human neutrophil elastase (HNE), by way of example and with preference sivelestat or DX-890 (Reltran);

compounds which inhibit the signal transduction cascade, in particular from the group of the tyrosine kinase inhibitors, by way of example and with preference dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib or tandutinib;

Rho kinase inhibitors, by way of example and with preference fasudil, Y-27632, SLx-2119, BF66851, BF-66852, BF-66853, KI-23095 or BA-1049;

anti-obstructive agents as used, for example, for the therapy of chronic obstructive pulmonary disease (COPD) or bronchial asthma, by way of example and with preference, inhalatively or systemically administered beta-receptor mimetics (e.g. bedoradrine) or inhalatively administered antimuscarinergic substances;

anti-inflammatory and/or immunosuppressive agents as used, for example, for the therapy of chronic obstructive pulmonary disease (COPD), bronchial asthma or pulmonary fibrosis, such as, by way of example and with preference, systemically or inhalatively administered corticosteroids, flutiform, pirfenidone, acetylcysteine, azathioprine or BIBF-1120;

chemotherapeutics like those employed, for example, for the therapy of neoplasms in the lung or other organs;

active compounds used for the systemic and/or inhalative treatment of pulmonary disorders, for example for cystic fibrosis (alpha-1-antitrypsin, aztreonam, ivacaftor, lumacaftor, ataluren, amikacin, levofloxacin), chronic obstructive pulmonary disease (COPD) (LAS40464, PT003, SUN-101), acute respiratory distress syndrome (ARDS) and acute lung injury (ALI) (interferon-beta-1a, traumakines), obstructive sleep apnoea (VI-0521), bronchiectasis (mannitol, ciprofloxacin), bronchiolitis obliterans (cyclosporin, aztreonam) and sepsis (pagibaximab, Voluven, ART-123);

antithrombotic agents, by way of example and with preference from the group of the platelet aggregation inhibitors, the anticoagulants or the profibrinolytic substances;

hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active compounds altering lipid metabolism, for example and with preference from the group of the thyroid receptor agonists, cholesterol synthesis inhibitors, by way of example and preferably HMG-CoA reductase inhibitors or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists;

active compounds which inhibit neoangiogenesis, by way of example and with preference inhibitors of the VEGF and/or PDGF signalling pathways, inhibitors of the integrin signalling pathways, inhibitors of the angiopoietin-Tie signalling pathways, inhibitors of the PI3K-Akt-mTor signalling pathways, inhibitors of the Ras-Raf-Mek-Erk signalling pathway, inhibitors of the MAPK signalling pathways, inhibitors of the FGF signalling pathways, inhibitors of the sphingosine-1-phosphate signalling pathways, inhibitors of endothelial cell proliferation or apoptosis-inducing active ingredients;

active compounds which reduce vascular wall permeability (oedema formation), by way of example and with preference corticosteroids, inhibitors of the AFKl-Smadl/5 signalling pathway, inhibitors of the VEGF and/or PDGF signalling pathways, cyclooxygenase inhibitors, inhibitors of the kallikrein-kinin system or inhibitors of the sphingosine-1-phosphate signalling pathways; and/or active compounds which reduce damage to the retina under oxidative stress, by way of example and with preference inhibitors of the complement system, especially antagonists of the complement C5a receptor, or agonists of the $5-HT_{1A}$ receptor;

antioxidants and free-radical scavengers;

hypotensive active compounds, by way of example and with preference from the group of the calcium antagonists, angiotensin AII antagonists, ACE inhibitors, beta-receptor blockers, alpha-receptor blockers, diuretics, phosphodiesterase inhibitors, sGC stimulators, cGMP elevators, aldosterone antagonists, mineralocorticoid receptor antagonists, ECE inhibitors and vasopeptidase inhibitors;

antidiabetics, by way of example and with preference from the group of the insulins and insulin derivatives, sulfonylureas, biguanides, meglitinide derivatives, glucosidase inhibitors, PPAR-gamma agonists, GLP 1 receptor agonists, glucagon antagonists, insulin sensitizers, CCK1 receptor agonists, leptin receptor agonists, potassium channel antagonists and the inhibitors of hepatic enzymes that are involved in the stimulation of gluconeogenesis and/or glycogenolysis;

anti-infectives, by way of example and with preference from the group of the antibacterial, antifungal and/or antiviral active substances; and/or substances for treatment of glaucoma, by way of example and with preference from the group of the adrenergics, beta-blockers, carbonic anhydrase inhibitors, parasympathomimetics and prostaglandins.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1 receptor blocker, by way of example and with preference prazosin.

In a preferred embodiment of the invention, the compounds of the invention are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference fiirosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

natriuretic peptides, for example atrial natriuretic peptide (ANP, anaritide), B-type natriuretic peptide or brain natriuretic peptide (BNP, nesiritide), C-type natriuretic peptide (CNP) and urodilatin;

inhibitors of endopeptidases (NEP inhibitors) such as sacubitril, omapatrilate or AVE-7688, or in dual combination ('ARNIs') with angiotensin receptor blockers (e.g. valsartan), e.g. LCZ696.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-5294/4), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include inter alia preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral and intravenous administration.

The compounds according to the invention can be converted to the administration forms mentioned. This can be accomplished in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctors.

In general, it has been found to be advantageous in the case of parenteral administration to administer amounts of about 0.001 to 1 mg/kg, preferably about 0.01 to 0.5 mg/kg body weight to achieve effective results. In the case of oral administration the dosage is about 0.01 to 100 mg/kg, preferably about 0.01 to 20 mg/kg and most preferably 0.1 to 10 mg/kg body weight.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples. Unless stated otherwise, the percentages in the tests and examples which follow are percentages by weight; parts are parts by weight. Solvent ratios, dilution ratios and concentration data for liquid/liquid solutions are based in each case on volume.

EXPERIMENTAL SECTION

Abbreviations and Acronyms:
abs. absolute
acac acetylacetonato
BINAP (2,2'-bis(diphenylphosphino)-1,1'-binaphthyl)
cat. catalytic
CI chemical ionization (in MS)
coe cyclooctene
d day(s)
TLC thin layer chromatography
DCM dichloromethane
DMA dimethylacetamide
DMF dimethylformamide
DMSO dimethyl sulfoxide
ee enantiomeric excess
EI electron impact ionization (in MS)
ent enantiomer/enantiomerically pure
eq equivalent(s)
ESI electrospray ionization (in MS)
EtOAc ethyl acetate
GC-MS gas chromatography-coupled mass spectrometry
% by weight percent by weight
h hour(s)
HPLC high-pressure, high-performance liquid chromatography
ID internal diameter
iPrOAc isopropyl acetate
iPrOH isopropanol
conc. concentrated
LC-MS liquid chromatography-coupled mass spectrometry
LDA lithium diisopropylamide
LiHMDS lithium bis(trimethylsilyl)amide
min minute(s)
MS mass spectrometry
MTBE 2-methoxy-2-methylpropane
NMR nuclear magnetic resonance spectrometry
NMP N-methyl-2-pyrrolidone
Ph phenyl
pTsOH p-toluenesulfonic acid
$R_f$ retention index (in TLC)
RP-HPLC reversed phase high performance liquid chromatography
RRT relative retention time
$R_t$ retention time
RT room temperature
TESCl chlorotriethylsilane
THF tetrahydrofuran
v/v volume to volume ratio (of a solution)
aq. aqueous, aqueous solution HPLC, LC-MS and GC-MS Methods:

Method A:

Instrument: Thermo Fisher-Scientific DSQ; chemical ionization; reactant gas NH3; source temperature: 200° C.; ionization energy 70 eV.

Method B:

Instrument: Micromass GCT, GC6890; column: Restek RTX-35, 15 m×200 µm×0.33 µm; constant helium flow rate: 0.88 ml/min; oven: 70° C.; inlet: 250° C.; gradient: 70° C., 30° C./min→310° C. (maintain for 3 min).

Method C:

Instrument: Thermo DFS, Trace GC Ultra; column: Restek RTX-35, 15 m×200 µm×0.33 µm; constant helium flow rate: 1.20 ml/min; oven: 60° C.; inlet: 220° C.; gradient: 60° C., 30° C./min→300° C. (maintain for 3.33 min).

Method D:

MS instrument type: Thermo Scientific FT-MS; instrument type UHPFC+: Thermo Scientific UltiMate 3000; column: Waters, HSST3, 2.1×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method E:

Instrument/detector high-performance liquid chromatograph with temperature-controlled column oven, UV detector and data evaluation system. Measurement wavelength: 226, bandwidth: 6 nm, column temperature 15° C., column: Chiralpak IA, length: 250 mm, internal diameter: 4.6 mm, particle size: 5 µm, mobile phase: A: 98% n-heptane+0.1% trifluoroacetic acid, B: 2% isopropanol+0.1% trifluoroacetic acid, flow rate: 1.0 ml/min, run time 20 min equilibration: 1 min, test solution about 2 mg/ml of the substance dissolved in isopropanol, injection volume 10 µl. Isomer 3 (main component): 14.39 min (RRT 1.00) isomer 1 (enantiomer): 12.35 min (RRT 0.86) isomer 2: 12.75 min (RRT 0.89), isomer 4: 16.13 min (RRT 1.12).

Method F:

Instrument: Thermo Scientific DSQII, Thermo Scientific Trace GC Ultra; column: Restek RTX-35MS, m×200 μm×0.33 μm; constant helium flow rate: 1.20 ml/min; oven: 60° C.; inlet: 220° C.; gradient: 60° C., 30° C./min→300° C. (maintain for 3.33 min).

Method G:

Instrument: Waters ACQUITY SQD UPUC System; column: Waters Acquity UPUC HSS T3 1.8 μm 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method H:

Stationary phase: Zorbax SB-AQ (length 100 mm, ID 2.1 mm, particle size 1.8 μm); mobile phase A: 2 ml of 70% strength perchloric acid/1 l of water; mobile phase B: acetonitrile; UV detection at 210 nm; oven temperature: 45° C., injection volume: 1.5 μl; flow rate: 1.0 ml/min; linear gradient in 4 steps: 8% B→15% B (0.70 min), 15% B→42% B (0.30 min), 42% B→57% B (2.20 min), 57% B→100% B (1.80 min), 1.00 min isocratic at 100% B;

Method I:

Stationary phase: Chiralpak AD-H (length 250 mm, ID 4.6 mm, particle size 5 μm); mobile phase: 0.2 ml of trifluoroacetic acid/1 ml of water/100 ml of 2-propanol/900 ml of isohexane; UV detection at 220 nm; oven temperature: 30° C., injection volume: 5 μl; flow rate: 1.25 ml/min; isocratic (20 min);

Starting Materials and Intermediates

Example 1

Methyl (4-chlorophenyl)acetate

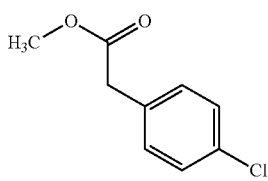

At room temperature, 1000.0 g of 4-chlorophenylacetic acid were added to 10 ml of concentrated sulfuric acid (95-97%) in 2.4 l of methanol, the solution was heated to 60° C. and stirred at this temperature for 2 h. The solution was cooled to room temperature and 200.0 g of sodium bicarbonate were added. 2050 ml of methanol were distilled off at 150 to 120 mbar, 2210 ml of toluene and 2100 ml of water were added to the residue and the phases were separated. The organic phase was washed with a solution of 50 g of sodium bicarbonate in 1000 ml of water, washed twice with in each case 600 ml of water and then concentrated to give an oil.

Yield: 1123.2 g (103.8% of theory). According to the NMR, the product contains about 3% toluene.

$^1$H-NMR (400 MHz, CDCl$_3$): 3.59 (s, 2H); 3.69 (s, 3H); 7.20-7.80 (m, 4H).

GC-MS (Method B) R$_t$=4.06 min; 184.0 [M]$^+$.

Example 2

Methyl 2-(4-chlorophenyl)-4,4,4-trifluoro-3-hydroxy-3-methylbutanoate (diastereomer mixture)

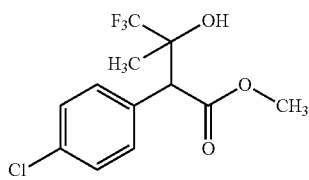 [SMILES: COC(=O)C(c1ccc(Cl)cc1)C(C)(O)C(F)(F)F]

Method A:

1489.5 ml (2.38 mol, 1.1 eq) of n-butyllithium (1.6 N) in hexane were cooled to −10° C. and 402.1 g (2.49 mol, 1.15 eq) of hexamethyldisilazane were added at −10 to −3° C. over 1.5 h. The resulting suspension was stirred at −6° C. for 10 min, 600 ml of tetrahydrofuran were added and the mixture was cooled to −72° C. Over 90 min, 400.0 g (2.17 mol) of methyl (4-chlorophenyl)acetate were added at at most −65° C. and the mixture was stirred at −78° C. for 0.5 h. A solution of 375.4 g (3.25 mol, 1.5 eq) of 1,1,1-trifluoroacetone in 400 ml of tetrahydrofuran was added over 2.5 h and the mixture was stirred for 10 min. 1000 ml (5 mol) of hydrochloric acid (5N) were then added over 5 min at at most 0° C. and the mixture was warmed to 22° C. and stirred for 0.5 h. The phases were separated and the organic phase was washed with 500 ml of water and concentrated under reduced pressure at 50° C. to give an oil.

Yield: 605.0 g (94.1% of theory)

The substance is present as a diastereomer mixture.

$^1$H-NMR (400 MHz, CDCl$_3$): 1.02 (s, 1.9H); 1.55 (s, 1.1H); 1.60 (br. S, 0.4H); 3.60 (s, 0.3H); 3.72 (s, 3H); 3.78 (s, 0.7H); 3.94 (s, 0.3H) 5.48 (s, 0.6H) 7.30-7.40 (m, 4H).

GC-MS (Method C) R$_t$=4.52 min, 296.0 [M]$^+$; 4.84 min, 296.0 [M]$^+$.

Method B:

In a stirred tank, 59.5 kg (0.140 kmol) of n-butyllithium (1.6 M in hexane) were cooled to 0° C., and 23.6 kg (0.146 kmol) of hexamethyldisilazane were metered in. Stirring was continued for 10 min and 21.4 kg of tetrahydrofuran were metered in. At −70° C., 24.0 kg (0.127 kmol) of methyl chlorophenylacetate were metered in and the reaction mixture was stirred for 3 h. A solution of 25.0 kg (0.218 kmol) of trifluoroacetone in 20.9 kg of tetrahydrofuran was then metered in at −70° C., the temperature of the reaction mixture was adjusted to −2° C. and 30.0 kg of water were metered in. At 10° C., 5.3 kg of ethyl acetate were added and the phases were separated. The organic phase was washed with 0.9 kg of sodium bicarbonate in 35.2 kg of water and then with 17.6 kg of water and 29.8 kg of hydrochloric acid (16.9% strength) and 14.7 kg of water. The organic phase was concentrated at 180 to 100 mbar and a jacket temperature of 40° to 50° C. and the oily product was withdrawn.

Yield: 30.6 kg, 84% pure based on the evaporation residue (68% of theory)

A sample was concentrated under reduced pressure and the evaporation residue was determined to be 84% pure.

MS (DCI) (Method A): 297.1 [M+H]$^+$; 314.1 [M+NH4]$^+$.

Example 3

Methyl 2-(4-chlorophenyl)-4,4,4-trifluoro-3-methyl-but-2-enoate (isomer mixture)

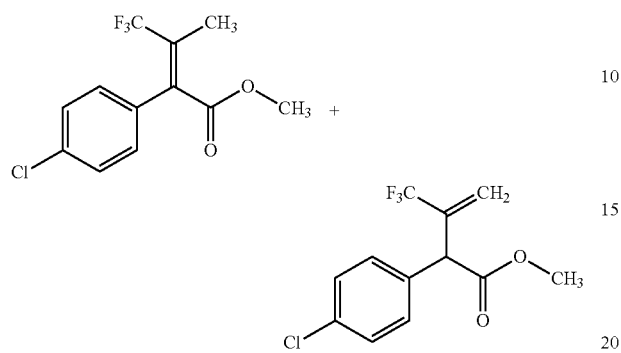

In a stirred tank, 151.3 kg of pyridine and 59.5 kg (0.170 kmol) of methyl 2-(4-chlorophenyl)-4,4,4-trifluoro-3-hydroxy-3-methylbutanoate were initially charged and volatile fractions were distilled off at 50 mbar until a bottom temperature of 38° C. had been reached. At 20° C., 39.1 kg (0.306 kmol) of phosphorus oxychloride were metered in. The mixture was heated to reflux temperature and stirred for a further 1.5 h. The mixture was cooled to 80° C. and 112 kg of water were metered in (highly exothermic). At 20° C., 151.4 kg of ethyl acetate were added and the separated organic phase was washed with 38.9 kg of hydrochloric acid (3.6% strength) and 38.2 kg of water and concentrated at 60 to 30 mbar and a jacket temperature of 45° C. to 55° C. 26.7 kg of tetrahydrofuran were added to the residue and the solution was withdrawn.

Yield: 37.5 kg of solution, yield about 79% of theory

The product consists of an isomer mixture.

GC MS (Method B) $R_t$=3.93 min, 278.1 [M]$^+$; 3.97 min, 278.1 [M]$^+$; 4.12 min, 278.1 [M]$^+$;

Example 4

Methyl 2-(4-chlorophenyl)-4,4,4-trifluoro-3-methyl-but-3-enoate (diastereomer mixture)

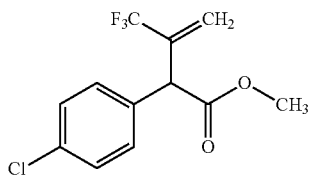 [SMILES: C=C(C(C(=O)OC)c1ccc(Cl)cc1)C(F)(F)F]

In a stirred tank, 57.8 kg (0.136 kmol) of n-butyllithium (1.6 M in hexane) were cooled to 0° C., and 51.1 kg of tetrahydrofuran were added. 15.3 kg (0.150 kmol) of diisopropylamine were metered in and the mixture was cooled to −75° C. At this temperature, a solution of 18.9 kg (0.068 kmol) of methyl 2-(4-chlorophenyl)-4,4,4-trifluoro-3-methylbut-2-enoate (isomer mixture) in 19 kg of tetrahydrofuran was metered in and the reaction mixture was stirred for 1 h. A solution of 16.3 kg (0.272 kmol) of acetic acid in 32.6 kg of tetrahydrofuran was then metered in. At 10° C., 72.5 kg of water and 65.3 kg of ethyl acetate were added, 54.8 kg of hydrochloric acid (18% strength) were metered in and the phases were separated. The organic phase was concentrated at 30 mbar and a jacket temperature of 60° C. The residue (18.4 kg) was diluted with 3.7 kg of polyethylene glycol 400 and the product was distilled on a thin-film evaporator at a jacket temperature of 145° C./1 to 10 mbar.

Yield: 13.6 kg (72% of theory)

GC-MS (Method B) $R_t$=3.98 min, 278.1 [M]$^+$.

Example 5

Methyl 2-(4-chlorophenyl)-4,4,4-trifluoro-3-methylbutanoate (diastereomer mixture)

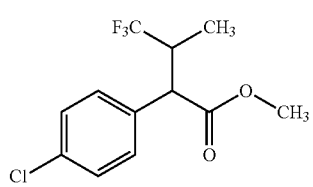 [SMILES: COC(=O)C(c1ccc(Cl)cc1)C(C)C(F)(F)F]

0.5 kg of catalyst (5% platinum on carbon, 50% water-wet) was added to a solution of 7.3 kg (0.026 kmol) of methyl 2-(4-chlorophenyl)-4,4,4-trifluoro-3-methylbut-3-enoate (XXIII) in 7.0 kg of methanol, and the mixture was hydrogenated at 50° C./80 bar. The catalyst was filtered off and the solution was withdrawn.

GC MS (Method B) $R_t$=4.00 min, 280.1 [M]$^+$; 4.03 min, 280.1 [M]$^+$.

Example 6 rel-(2R,3S)-2-(4-Chlorophenyl)-4,4,4-trifluoro-3-methylbutanoic acid (enantiomer mixture)

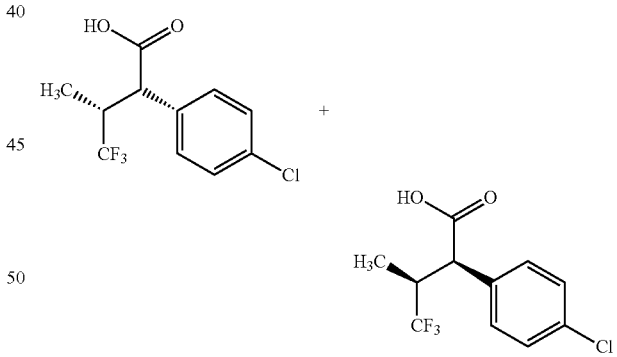

At 20° C., 22.9 kg (0.127 kmol) of 30% sodium methoxide in methanol were metered into a solution of 19.8 kg (0.071 kmol) of methyl 2-(4-chlorophenyl)-4,4,4-trifluoro-3-methylbutanoate in 36.3 kg of methanol and the mixture was stirred for 1.5 h. 118.7 kg of water were then metered in, the mixture was stirred for 0.5 h and low-boilers were distilled off up to a bottom temperature of 97° C. During the distillation, 29.7 kg of water were metered in. The mixture was cooled to 5° C. and the precipitated solid was isolated and washed with 16 kg of cold water. The moist product was suspended in 91.3 kg of water, 13.1 kg of hydrochloric acid (20% strength) were metered in at 20° C. and the suspension was stirred for 2 h. The solid was isolated, washed with 38.8 kg of water and dried under reduced pressure at a jacket temperature of 50° C. using nitrogen carrier gas.

Yield: 10.1 kg (53.5% of theory)

$^1$H-NMR (400 MHz, DMSO-$d_6$): 0.78 (d, 3H); 0.89 (m, 2H); 3.14-3.39 (m, 1H); 3.68 (m, 1H); 7.29-7.55 (m, 4H); 12.82 (br. s, 1H).

LC-MS (Method D) $R_t$=1.85 min, 265.0243 [M–H]$^-$.

Example 7

(2S,3R)-2-(4-Chlorophenyl)-4,4,4-trifluoro-3-methylbutanoic acid—quinine salt

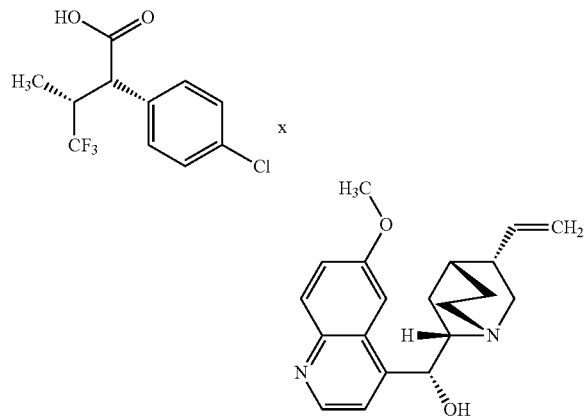

At reflux temperature, a solution of 19.3 kg (0.072 kmol) of rel-(2R,3S)-2-(4-chlorophenyl)-4,4,4-trifluoro-3-methylbutanoic acid in 92.5 kg of ethanol was metered into 17.6 kg (0.054 kmol) of quinine in 173.8 kg of ethanol and the mixture was stirred for 10 min. Over a period of 2.5 h, the mixture was cooled to 0° C. and stirred at this temperature for 1 h and the solid was isolated and washed with 69 kg of ethanol and 33.3 kg of water. The filter cake was then heated to reflux temperature in 236.3 kg of water and 630.9 kg of methanol and stirred for 0.5 h. The mixture was then cooled to 0° C. over a period of 5 h and stirred for 1 h and the solid was isolated and washed with a solution of 20.3 kg of methanol and 7.6 kg of water and then with 33.3 kg of water. The filter cake was then heated to reflux temperature in 98.3 kg of water and 481.4 kg of ethanol and stirred for 0.5 h. The mixture was then cooled to 0° C. over a period of 5 h and stirred for 1 h and the solid was isolated and washed with a solution of 21 kg of methanol and 6.6 kg of water and then with 33.3 kg of water and dried under reduced pressure (30 mbar) at a jacket temperature of 50° C. using nitrogen carrier gas.

Yield: 15.5 kg (35.3% of theory)

$^1$HNMR (400 MHz, DMSO-$d_6$): 0.77 (d, 3H); 1.50-1.84 (m, 5H); 2.21-2.37 (m, 1H); 2.54-2.74 (m, 1H); 2.96-3.08 (m, 1H); 3.08-3.42 (m, 13H incl. $H_2O$); 3.62 (d, 1H); 3.88 (s, 3H); 4.87-5.06 (m, 2H); 5.31-5.43 (m, 1H); 5.79-5.94 (m, 1H); 5.77 (br. s, 1H); 7.33-7.44 (m, 5H); 7.46-7.56 (m, 2H); 7.93 (d, 1H); 8.69 (d, 1H).

LC-MS (Method D) $R_t$=0.80 min 325.1 [M+H]$^+$ (quinine); 1.85 min 531.0 [2M–H]$^-$ 265.0 [M–H]$^-$ 221.0 [M-CO$_2$—H]$^-$ (2-(4-chlorophenyl)-4,4,4-trifluoro-3-methylbutanoic acid).

HPLC (Method E): 99.5% ee

Example 8

(2S,3R)-2-(4-Chlorophenyl)-4,4,4-trifluoro-3-methylbutanoic acid

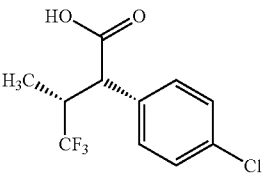

At 20° C., 27.8 kg (0.190 kmol) of hydrochloric acid (25% strength) were metered into 32.1 kg (0.053 kmol) of (2S,3R)-2-(4-chlorophenyl)-4,4,4-trifluoro-3-methylbutanoic acid—quinine salt (1:1) in 268 kg of water and the mixture was stirred for 2.5 h. The solid was isolated and washed with 82.5 kg of water and dried under reduced pressure (30 mbar) at a jacket temperature of 50° C. using nitrogen carrier gas.

Yield: 14.4 kg (100% of theory)

HPLC (Method E): 99.1% ee $^1$H NMR (400 MHz, DMSO-$d_6$) 0.78 (d, 3H) 3.11-3.38 (m, 1H); 3.68 (d, 1H); 7.29-7.54 (m, 4H); 12.83 (br s, 1H).

LC-MS (Method D) $R_t$=1.85 min 265.0 [M–H]$^-$.

Example 9 tert-Butyl (2E)-3-cyclopropylprop-2-enoate

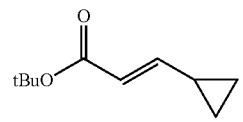 [SMILES: CC(C)(C)OC(=O)/C=C/C1CC1]

KOtBu (384 g, 3.42 mol) was suspended in 4 l of toluene, and tert-butyl (diethoxyphosphoryl)acetate (864 g, 3.42 mol) was added at 15° C. to 30° C. After 1 h, the mixture was cooled to 0° C. and dissolved in cyclopropanecarbaldehyde (200 g, 2.85 mol) dissolved in 800 ml of toluene. The mixture was stirred for another 2 h and 5 l of NH$_4$Cl solution (20%) were then added. The organic phase was separated off, washed with 4 l of NaCl solution (20%) and concentrated. The precipitated solid was filtered off, washed with a small amount of cold toluene and dried under reduced pressure, giving 286 g of a solid (yield 60% of theory).

GC MS (Method F) $R_t$=1.21 min, M$^+$=168.1;

$^1$H-NMR (500 MHz, d6-DMSO): 0.63 (m, 2H); 0.89 (m, 2H); 1.41 (s, 9H); 1.60 (m, 1H); 5.82 (d, 1H); 6.28 (dd, 1H).

Example 10 tert-Butyl 3-(3-amino-4-chlorophenyl)-3-cyclopropylpropanoate 4-methylbenzenesulfonate

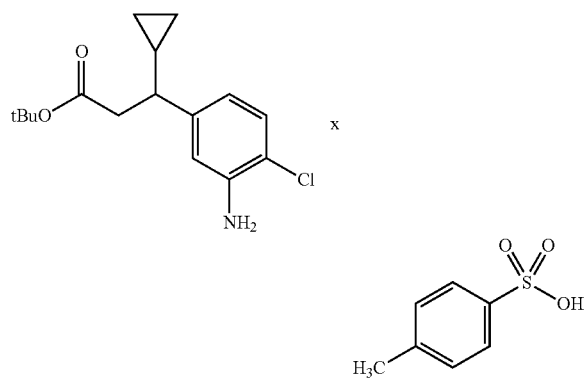

(+,−)-BINAP (29 g, 0.00575 eq) and [Rh(COD)Cl]$_2$ (9.8 g, 0.0025 eq) in 1 l of THF were stirred exposed to the air for 15 min. In another vessel, 1.33 kg of tert-butyl (2E)-3-cyclopropylprop-2-enoate (7.92 mol), 630 g of KOH (9.51 mol), 2.21 kg of pinacol 3-amino-4-chlorophenylboronate (8.72 mol) and 9.7 ml of 1,5-cyclooctadiene (0.01 eq) were suspended under nitrogen in a mixture of 9.3 l of THF and 730 ml of iPrOH. This mixture was heated to 60° C. and the catalyst mixture was added. The mixture was stirred at this temperature for a further 9 h. The reaction mixture was cooled to 0° C. and 8 l of water were added. The phases were separated and the aqueous phase was extracted with 2.7 l of EtOAc. The combined organic phases were washed with 2.7 l of concentrated NaCl solution. This solution was returned to the vessel and 2.11 kg (11.1 mol) of pTsOH were added a little at a time at 15° C. to 20° C. After 1 h, the suspension was filtered and the product was washed with EtOAc and dried under reduced pressure, giving 3.4 kg (93% of theory) of a solid.

$^1$H-NMR (500 MHz, d6-DMSO): 0.07 (m, 1H); 0.21 (m, 1H); 0.32 (m, 1H); 0.50 (m, 1H); 0.93 (m, 1H); 1.28 (s, 9H); 2.11 (m, 1H); 2.29 (s, 3H); 2.49 (dd, 1H); 2.59 (dd, 1H); 6.54 (d, 1H); 6.73 (d, 1H); 7.12 (m, 3H); 7.47 (d, 2H).

Example 11

3-(3-Amino-4-chlorophenyl)-3-cyclopropylpropanoic acid

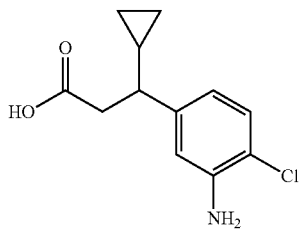 [SMILES: Nc1cc(C(CC(=O)O)C2CC2)ccc1Cl]

At 22° C., 1.90 kg of tert-butyl 3-(3-amino-4-chlorophenyl)-3-cyclopropylpropanoate 4-methylbenzenesulfonate and 154 g of pTsOH (0.2 eq) were suspended in 3.8 l of HOAc. The suspension was heated to 60° C. and stirred for 1 h. The reaction mixture was cooled to 0° C., 8.6 l of water were added and the pH was adjusted to pH=12 using 6.5 kg of concentrated aqueous sodium hydroxide solution (45%) NaOH. The aqueous phase was extracted twice with iPrOAc (3.8 l and 0.8 l). Concentrated aqueous hydrochloric acid (32% strength) was added to the aqueous solution, and 3.5 l of DCM were added. The phases were separated and the organic phase was washed with 0.8 l of water. The crude solution was used for the subsequent crystallization.

For crystallization, three crude solutions were combined. The DCM was removed under reduced pressure and 2.9 l of methylcyclohexane were added. The suspension was concentrated and 2.9 l of methylcyclohexane were added. This operation was repeated, with removal of methylcyclohexane under reduced pressure and addition of a further 2.9 l. After the last addition of methylcyclohexane, the methylcyclohexane was removed under reduced pressure and 0.6 l of DCM and 0.6 l of methylcyclohexane were added. At 45° C., the solution was seeded with 2 g of crystalline product. The suspension was cooled to 0° C., washed with methylcyclohexane and dried under reduced pressure, giving 2.23 kg (78% of theory) of a solid.

$^1$H-NMR (500 MHz, d6-DMSO): 0.07 (m, 1H); 0.21 (m, 1H); 0.31 (m, 1H); 0.48 (m, 1H); 0.92 (m, 1H); 2.11 (m, 1H); 2.55 (dd, 1H); 2.61 (dd, 1H); 6.44 (dd, 1H); 6.65 (d, 1H); 7.06 (d, 1H).

Example 12

(3S)-3-(3-Amino-4-chlorophenyl)-3-cyclopropylpropanoic acid (1S,2R)-1-amino-2,3-dihydro-1H-inden-2-ol

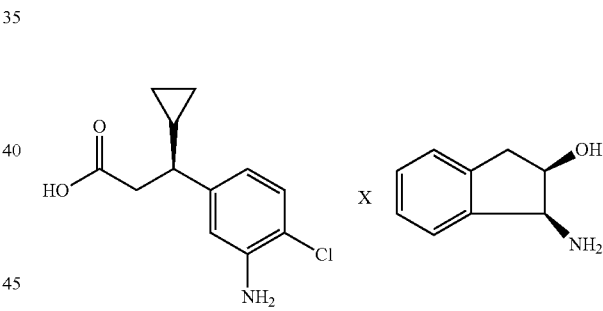

1.40 kg of 3-(3-amino-4-chlorophenyl)-3-cyclopropylpropanoic acid were suspended in 15.5 kg of acetonitrile and 1 l of water. The mixture was heated to 60° C. and 0.7 kg of (1S,2R)-(−)-cis-1-amino-2-indanol was added. The reaction mixture was seeded and, over 5 h, slowly cooled to 22° C. The product was filtered off, suspended in 12 kg of acetonitrile and 0.8 l of water and heated to 75° C. More acetonitrile and water 3.8 l (9.5:0.5; ACN:water) were added until a clear solution had formed. The solution was seeded with crystalline product and the suspension was, over 6 h, cooled to 22° C. The suspension was cooled to 0° C., stirred for 1 h, filtered and washed with acetonitrile. The indanol salt formed was dried under reduced pressure, giving 880 g (39% of theory) of a solid.

HPLC MS (Method G) R$_t$=0.84 min, MH$^+$=240.1;

$^1$H-NMR (500 MHz, d6-DMSO): 0.06 (m, 1H); 0.21 (m, 1H); 0.30 (m, 1H); 0.47 (m, 1H); 0.90 (m, 1H); 2.15 (q, 1H); 2.48 (m, 2H); 2.78 (d, 1H); 2.96 (dd, 1H); 4.12 (s, 1H); 4.28 (s, 1H); 6.45 (d, 1H); 6.66 (d, 1H); 7.05 (d, 1H); 7.18 (m, 3H); 7.34 (m, 1H).

Example 13

(3S)-3-(3-Amino-4-chlorophenyl)-3-cyclopropylpropanoic acid hydrochloride

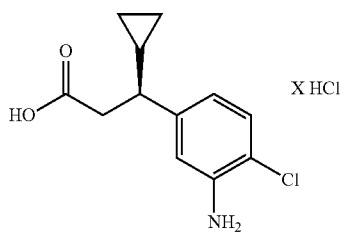

For salt resolution, several batches of the indanol salt were combined. 1.35 kg of (3S)-3-(3-amino-4-chlorophenyl)-3-cyclopropylpropanoic acid indanol salt were suspended in 13.5 l of EtOAc and 6.75 l of water, and 610 ml of HCl (16% in water) were added. The phases were separated and the organic phase was washed twice with water (2×3.4 l of water), dried with sodium sulfate and concentrated, giving 860 g (100% of theory) of an oily product.

The free amino acid 860 g was dissolved in 1.9 l of EtOAc, and 900 ml of HCl in dioxane (4 M) were added. The product was filtered off, washed with EtOAc and dried, giving 936 g (94% of theory) of a solid having an enantiomeric purity of 99.4%.

HPLC MS (Method G) $R_t$=0.84 min, MH$^+$=240.1;
$^1$H-NMR (500 MHz, d6-DMSO): 0.09 (m, 1H); 0.23 (m, 1H); 0.32 (m, 1H); 0.50 (m, 1H); 0.93 (m, 1H); 2.16 (q, 1H); 2.55 (dd, 1H); 2.63 (dd, 1H); 6.64 (m, 1H); 6.84 (m, 1H); 7.17 (m, 1H).

Example 14

(3S)-3-(4-Chloro-3-{[(2S,3R)-2-(4-chlorophenyl)-4,4,4-trifluoro-3-methylbutanoyl]amino}phenyl)-3-cyclopropylpropanoic acid

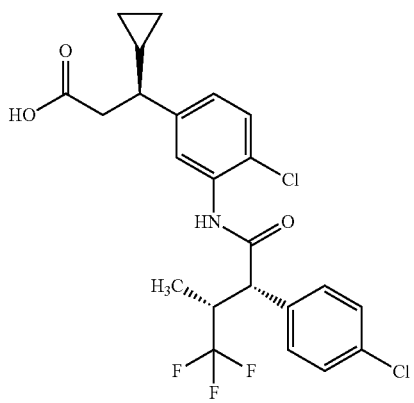 [SMILES: C[C@H]([C@H](C(=O)Nc1cc([C@@H](CC(=O)O)C2CC2)ccc1Cl)c1ccc(Cl)cc1)C(F)(F)F]

Method A:
(2S,3R)-2-(4-Chlorophenyl)-4,4,4-trifluoro-3-methylbutanoic acid (1.43 kg) was suspended in 6.6 kg of THF, and 28 g of DMF were added. At 20° C., oxalyl chloride (680 g) was added and stirring was continued for 45 min.

In another vessel, (3S)-3-(3-amino-4-chlorophenyl)-3-cyclopropylpropanoic acid hydrochloride (1:1) (1.48 kg) was suspended in 6.6 kg of THF, and 3.45 kg of diisopropylethylamine were added at 20° C. At this temperature, TESCl (1.05 kg) was added, and stirring was continued for 1 h.

At 0° C., the TES-protected amino acid was added slowly to the acid chloride, and the empty vessel was washed with 1 kg of THF. After 1.5 h of stirring, EtOAc (6.2 kg) and 2 N HCl (7.4 kg) were added, and the phases were separated. The organic phase was washed with a further 7.4 kg of 2 N HCl solution and washed twice with 7.4 kg of 10% strength NaCl solution in water. The solution was filtered and washed with EtOAc. The EtOAc was removed under reduced pressure, and 13.6 kg of heptane were added. The distillation was continued, and a further 5.5 kg of heptane were added. The reaction mixture was seeded at 55° C. and slowly cooled to 0° C. The product was filtered off, washed with heptane and dried under reduced pressure, giving 1.72 kg (67% of theory) of the desired product as a solid.

$^1$H-NMR (500 MHz, d6-DMSO): 0.07 (m, 1H); 0.23 (m, 1H); 0.28 (m, 1H); 0.49 (m, 1H); 0.80 (d, 3H); 0.94 (m, 1H); 2.24 (m, 1H); 2.56 (dd, 1H); 2.64 (dd, 1H); 3.37 (m, 1H); 4.13 (d, 1H); 7.10 (dd, 1H); 7.36 (d, 1H); 7.41 (d, 1H); 7.46 (m, 4H); 9.83 (s, 1H); 12.04 (s, 1H).

Method B:
tert-Butyl (3S)-3-(4-chloro-3-{[(2S,3R)-2-(4-chlorophenyl)-4,4,4-trifluoro-3-methylbutanoyl]amino}phenyl)-3-cyclopropylpropanoate (160 g) was dissolved in 2.2 kg of dioxane, and 670 g of HCl (32% in water) were added. The reaction mixture was heated to 50° C. and stirred for 12 h. After cooling to RT, 349 g of heptane and 844 g of water were added and the phases were separated. The aqueous phase was extracted with a mixture of 228 g of heptane and 495 g of MTBE. The organic phases were combined, washed with 1.3 kg of water and dried with sodium sulfate. Two of these batches were combined and the solvent was evaporated. At 40° C., the crude product was dissolved in 220 g of MTBE and 96 g of heptane. At 50° C., this solution was added slowly to 3897 g of heptane. The mixture was seeded with 1.5 g of product and slowly cooled to 0° C. The product was filtered off, washed with heptane and dried under reduced pressure, giving 250 g (88% of theory) as a solid.

$^1$H-NMR (500 MHz, d6-DMSO): 0.07 (m, 1H); 0.23 (m, 1H); 0.28 (m, 1H); 0.49 (m, 1H); 0.80 (d, 3H); 0.94 (m, 1H); 2.24 (m, 1H); 2.56 (dd, 1H); 2.64 (dd, 1H); 3.37 (m, 1H); 4.13 (d, 1H); 7.10 (dd, 1H); 7.36 (d, 1H); 7.41 (d, 1H); 7.46 (m, 4H); 9.83 (s, 1H); 12.04 (s, 1H).

Example 15 tert-Butyl (3S)-3-(3-amino-4-chlorophenyl)-3-cyclopropylpropanoate

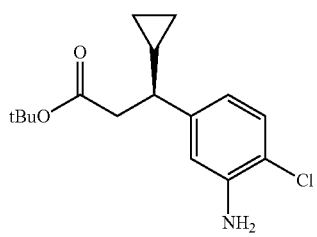 [SMILES: CC(C)(C)OC(=O)C[C@H](c1ccc(Cl)c(N)c1)C1CC1]

Under an atmosphere of nitrogen, 806 mg of (1S,4S)-2,5-diphenylbicyclo[2.2.2]octa-2,5-diene (3.12 mmol, 0.011 eq) and 1.16 g of [Rh(CH$_2$=CH$_2$)$_2$Cl]$_2$ (2.97 mmol, 0.01 eq) were stirred in 35 ml of MeOH for 30 min.

In another flask, under an atmosphere of nitrogen, 50 g (297 mmol) of tert-butyl (2E)-3-cyclopropylprop-2-enoate, 82.9 g (327 mmol) of pinacol (3-amino-4-chlorophenyl) boronate and 1.67 g of KOH (29.7 mmol) were suspended in MeOH (350 ml) and water (35 ml) and heated to 50° C. The catalyst solution was added and stirring was continued for 17 h. Water and EtOAc (150 ml) were added and the phases were separated. 73.5 g of pTsOH (386 mmol) were added to the organic phase and the solid formed was isolated, washed with EtOAc and dried under reduced pressure, giving 107 g (77% of theory) with an enantiomeric excess of 97.1%.

Example 16 tert-Butyl (3S)-3-(4-chloro-3-{[(2S,3R)-2-(4-chlorophenyl)-4,4,4-trifluoro-3-methylbutanoyl]amino}phenyl)-3-cyclopropylpropanoate

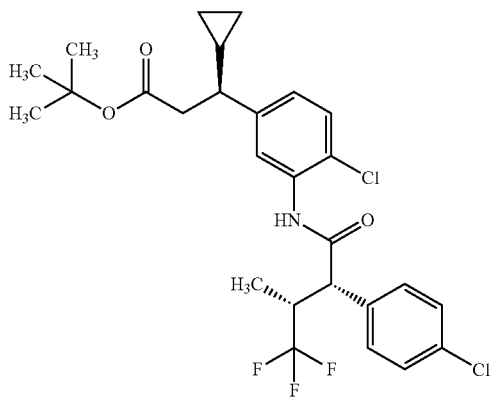 [SMILES: C[C@H]([C@H](C(=O)Nc1cc([C@@H](CC(=O)OC(C)(C)C)C2CC2)ccc1Cl)c1ccc(Cl)cc1)C(F)(F)F]

(2S,3R)-2-(4-Chlorophenyl)-4,4,4-trifluoro-3-methylbutanoic acid (104 g, 389 mmol) was suspended in 1 l of THF, and 2 ml of DMF were added. At 20° C., oxalyl chloride (54 g, 428 mmol) was added and stirring was continued for 45 min.

In another vessel, tert-butyl (3S)-3-(3-amino-4-chlorophenyl)-3-cyclopropylpropanoate (115 g, 389 mmol) was dissolved in 1 l of THF, and 114 m (3.89 mol) of pyridine were added at 20° C. At this temperature, the acid chloride was added slowly, and stirring was continued for 1 h. The reaction was quenched by addition of 800 ml of 20% strength citric acid, and the phases were separated. The organic phase was further washed with 800 ml of 20% strength citric acid and water (2×800 ml). The solvent was evaporated and the residue was dissolved in 160 ml of MTBE and 650 ml of heptane. The reaction mixture was concentrated to half its original volume and slowly cooled to RT. The product was filtered off, washed with heptane and dried under reduced pressure, giving 183 g (86% of theory) of a solid.

$^1$H-NMR (500 MHz, d6-DMSO): 0.07 (m, 1H); 0.22 (m, 1H); 0.30 (m, 1H); 0.50 (m, 1H); 0.80 (d, 3H); 0.94 (m, 1H); 2.20 (m, 1H); 2.52 (dd, 1H); 2.62 (dd, 1H); 3.36 (m, 1H); 4.13 (d, 1H); 7.11 (dd, 1H); 7.36 (d, 1H); 7.43 (d, 1H); 7.46 (m, 4H); 9.80 (s, 1H)

The invention claimed is:
1. A process for preparing the compound of the formula (I)

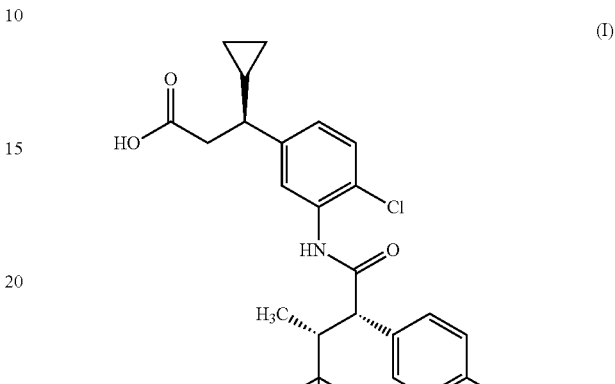

comprising reacting the compound of the formula (II)

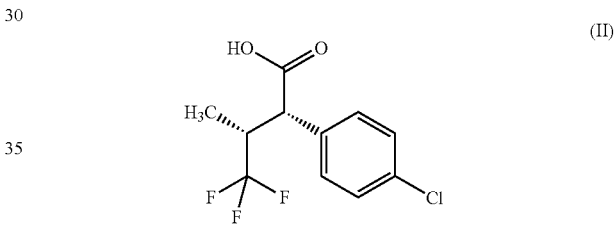

under base-free conditions and using an organosilicon compound with the compound of the formula (VII)

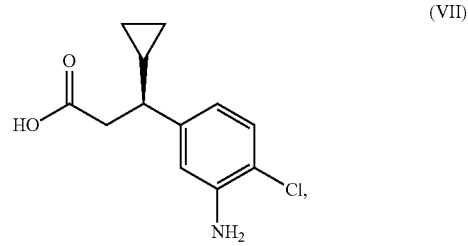 [SMILES: Nc1cc([C@@H](CC(=O)O)C2CC2)ccc1Cl]

or a salt of this compound,
and with removal of the silyl protective group in aqueous acidic solution converting into the compound of the formula (I).

* * * * *